(12) United States Patent
Dong et al.

(10) Patent No.: US 9,008,760 B2
(45) Date of Patent: Apr. 14, 2015

(54) SYSTEM AND METHOD FOR OFF-LINE ANALYSIS OF CARDIAC DATA

(75) Inventors: Yanting Dong, Lexington, KY (US); Shijie Zhang, Pittsburgh, PA (US); Deepa Mahajan, Circle Pines, MN (US); Chenguang Liu, Birmingham, AL (US); Dan Li, Shoreview, MN (US); Yayun Lin, St. Paul, MN (US); Derek D. Bohn, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 164 days.

(21) Appl. No.: 13/483,394

(22) Filed: May 30, 2012

(65) Prior Publication Data

US 2013/0138005 A1  May 30, 2013

Related U.S. Application Data

(60) Provisional application No. 61/491,453, filed on May 31, 2011.

(51) Int. Cl.
*A61B 5/04* (2006.01)
*A61B 5/0452* (2006.01)
*A61B 5/00* (2006.01)
*A61B 5/0245* (2006.01)
(Continued)

(52) U.S. Cl.
CPC .............. *A61B 5/0452* (2013.01); *A61B 5/7217* (2013.01); *A61B 5/0245* (2013.01); *A61B 5/042* (2013.01); *A61N 1/3704* (2013.01)

(58) Field of Classification Search
USPC ................................................. 600/508, 509
See application file for complete search history.

(56) References Cited

U.S. PATENT DOCUMENTS

| 6,112,119 A | 8/2000 | Schuelke et al. |
| 6,609,023 B1 | 8/2003 | Fischell et al. |
| 6,917,830 B2 | 7/2005 | Palreddy et al. |

(Continued)

FOREIGN PATENT DOCUMENTS

WO  2012166901  12/2012

OTHER PUBLICATIONS

"PCT International Search Report and Written Opinion", from International Application No. PCT/US2012/040186, corresponding to U.S. Appl. No. 13/483,387, mailed Sep. 5, 2012, pp. 1-13.

(Continued)

*Primary Examiner* — Christopher D Koharski
*Assistant Examiner* — Nadia A Mahmood
(74) *Attorney, Agent, or Firm* — Pauly, DeVries Smith & Deffner LLC

(57) ABSTRACT

A system and method for performing off-line analysis of cardiac electrogram data, comprising: retrieving an electrogram from a memory location; identifying a first-channel group of candidate beats from at least a first channel of the electrogram; and identifying a second-channel group of candidate beats from at least a second channel of an electrogram. For each first-channel beat candidate near a second-channel beat candidate, the amplitude of the first-channel beat candidate is compared with the amplitude of a previous beat and the amplitude of a next beat on the first electrogram channel, and first-channel beat candidates that are outside of a first pre-determined range from either the previous or next beat are removed. Then first-channel beat candidates that are outside of a second pre-determined range from either the previous or next beat candidate are removed.

14 Claims, 18 Drawing Sheets

(51) Int. Cl.
 *A61B 5/042* (2006.01)
 *A61N 1/37* (2006.01)

(56) References Cited

U.S. PATENT DOCUMENTS

| | | |
|---|---|---|
| 6,978,182 B2 | 12/2005 | Mazar et al. |
| 7,283,863 B2 | 10/2007 | Gunderson et al. |
| 2004/0106957 A1* | 6/2004 | Palreddy et al. .......... 607/9 |
| 2004/0260350 A1 | 12/2004 | Brandstetter et al. |
| 2008/0275519 A1 | 11/2008 | Ghanem et al. |
| 2010/0204745 A1 | 8/2010 | Li et al. |
| 2011/0077541 A1 | 3/2011 | Dong et al. |
| 2012/0271185 A1 | 10/2012 | Sanghera et al. |
| 2013/0138004 A1 | 5/2013 | Dong et al. |

OTHER PUBLICATIONS

"Communication Pursuant to Rules 161(1) and 162 EPC", for European Patent Application No. 12731213.0, mailed Jan. 24, 2014 (2 pages).

"International Preliminary Report on Patentability", for PCT/US2012/040186, mailed Dec. 2, 2013 (8 pages).

"Non-Final Office Action", for U.S. Appl. No. 13/483,387, mailed May 15, 2014 (13 pages).

* cited by examiner

SYSTEM AND METHOD FOR OFF-LINE ANALYSIS OF CARDIAC DATA

This application claims the benefit of U.S. Provisional Application No. 61/491,453, filed May 31, 2011, the contents of which are herein incorporated by reference.

TECHNICAL FIELD

This disclosure relates generally to systems and methods for analyzing data from a medical device, and more particularly, to medical systems and methods that can be used to analyze cardiac signal data.

SUMMARY OF THE INVENTION

Embodiments of the invention are related to medical systems and methods that can be used to analyze and collect information from implanted medical devices, amongst other things.

In one embodiment, a method for performing off-line analysis of cardiac electrogram data includes the steps of retrieving an electrogram from a memory location; identifying a first-channel group of candidate beats from at least a first channel of the electrogram; and identifying a second-channel group of candidate beats from at least a second channel of an electrogram. For each first-channel beat candidate near a second-channel beat candidate, the amplitude of the first-channel beat candidate is compared with the amplitude of a previous beat and the amplitude of a next beat on the first electrogram channel, and first-channel beat candidates that are outside of a first pre-determined range from either the previous or next beat are removed. For each first-channel beat candidate near a second-channel beat candidate, the amplitude of the first-channel beat candidate is compared with the amplitude of a previous beat candidate and the amplitude of a next beat candidate on the first electrogram channel, and first-channel beat candidates that are outside of a second pre-determined range from either the previous or next beat candidate are removed. A first-channel beat candidate is considered to be near a second-channel beat candidate if it occurs within a first time interval from the second-channel beat candidate.

In another embodiment, an off-line method for analyzing cardiac electrogram data includes the steps of retrieving an electrogram from a memory location; identifying an initial first-channel group of candidate beats from at least a first channel of the electrogram; and identifying a second-channel group of candidate beats from at least a second channel of an electrogram. For each initial first-channel beat candidate near a second-channel beat candidate, candidate beats from the group of initial first-channel candidate beats that do not meet a set of criteria are removed. Determining whether the candidates should be removed comprises comparing the amplitude of the initial first-channel beat candidate with an amplitude of a previous beat and an amplitude of a next beat on the first electrogram channel and removing initial first-channel beat candidates that are outside of a first pre-determined range from either the previous or next beat when the number of first-channel beat candidates that are outside of a first pre-determined range from either the previous or next beat exceeds a first pre-defined beat count threshold. An initial first-channel beat candidate is considered to be near a second-channel beat candidate if it occurs within a first time interval from the second-channel beat candidate.

In yet another embodiment, a system for off-line analysis of cardiac electrogram data comprises a memory location storing patient data comprising one or more electrograms from at least a first channel and a second channel; and an external computing device configured to retrieve the patient data from the memory location. The external computing device comprises a database module comprising memory for storing the patient data; and an analysis module configured to identify a first-channel group of candidate beats from at least a first channel of the electrogram and a second-channel group of candidate beats from at least a second channel of the electrogram. The external computing device is further configured to compare the amplitude of a first-channel beat candidate with the amplitude of a previous beat and the amplitude of a next beat on the first electrogram channel and remove first-channel beat candidates that are outside of a first pre-determined range from either the previous or next beat for each first-channel beat candidate near a second-channel beat candidate. The external computing device is further configured to compare the amplitude of the first-channel beat candidate with the amplitude of a previous beat candidate and the amplitude of a next beat candidate on the first electrogram channel and remove first-channel beat candidates that are outside of a second pre-determined range from either the previous or next beat candidate for each first-channel beat candidate near a second-channel beat candidate. A first-channel beat candidate is considered to be near a second-channel beat candidate if it occurs within a first time interval from the second-channel beat candidate.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE DRAWINGS

The invention may be more completely understood in connection with the following drawings, in which.

Figure 1:
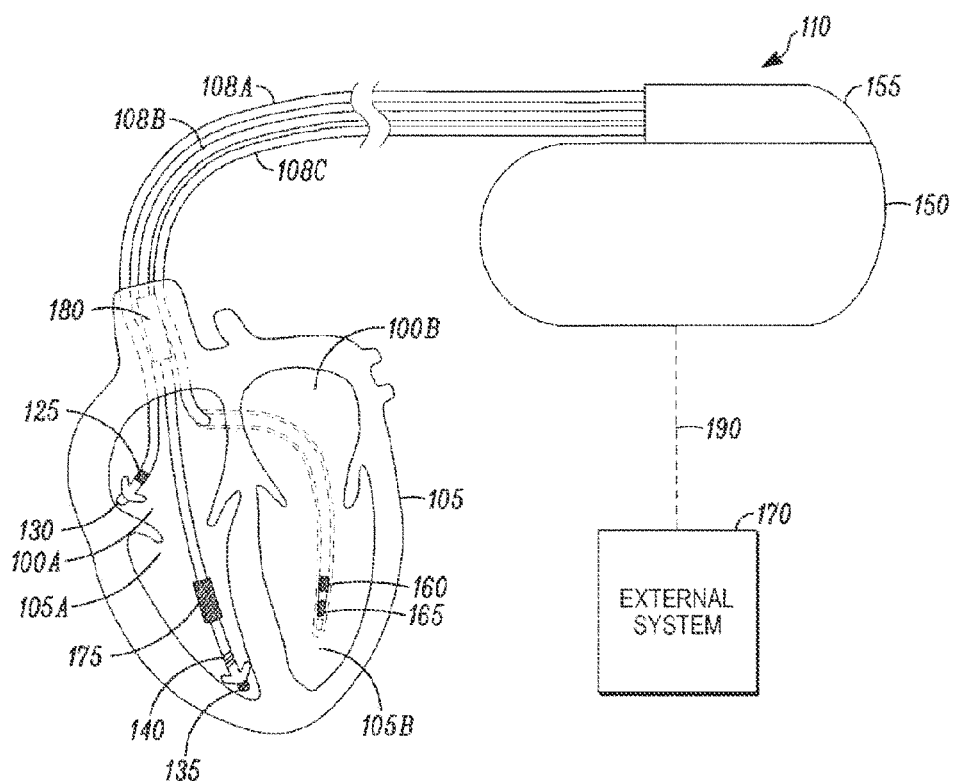
FIG. 1 is an illustration of portions of a system that use an implantable medical device.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION

This disclosure relates generally to medical data-generating devices and, more particularly, to systems and methods for analyzing information from such medical devices. In particular, this disclosure relates to systems and methods for performing analysis on cardiac signals to detect oversensing, undersensing, and noise by a particular data-generating device or analysis method. Methods of detecting heart beats on at least one channel are used to output a group of candidate beats. The candidate beats can then be used in combination with far-field sensing removal techniques described herein, so that there is more confidence that the remaining beats are actual heart beats. Far-field sensing is sensing of signals from distant ventricular activity that is detected by the atrial lead.

The heart pumps oxygen-rich blood through the arteries to tissues, including organs, muscles, and nerves. The cardiac conduction system includes specialized cardiac muscle cells in the walls of the heart that send signals to the heart muscle causing it to contract. The main parts of the cardiac conduction system are the SA node, AV node, bundle of His, bundle branches, and Purkinje fibers. The normal pattern of a heart beat begins when electrical signals are conducted to the top chambers of the heart, the left atrium and right atrium. The SA node starts the process by causing the atrial muscles to contract, pushing blood into the two lower chambers, the left ventricle and right ventricle. Then, the electrical signal travels to the AV node, through the bundle of His, down the bundle branches, and through the Purkinje fibers, causes the ventricles to contract, pushing blood to the heart and the rest of the body. This signal creates an electrical current that can be seen on an electrogram or electrocardiogram.

Methods for performing independent, off-line evaluation of event sensing for collected electrograms are used, which utilize electrogram (EGM) data from an implantable medical device (IMD). The IMD determines locations of heart beats within the EGM data, resulting in a group of device-identified beat locations. These may also be known as device markers. The EGM data and device-identified beat locations are stored in a memory location. Next, a computer or other computing device such as a programmer is used to retrieve the EGM data and device-identified beat locations from the memory location. The computing device determines the locations of heart beats on at least one channel of EGM data using a multi-pass process. The group of beat locations determined using this multi-pass process is referred to as the multi-pass group of beat locations. The computing device analyzes and compares the device-identified group of beat locations with the multi-pass group of beat locations. Based on the comparison, the presence of oversensing, undersensing, or noise can potentially be confirmed in the device-identified beat locations.

Cardiac signals can be in the form of EGMs, heart sound signals, impedance signals, and pressure signals. Data-generating devices include IMDs, while in some embodiments the data generating devices are external or subcutaneous. In some embodiments, the information gathered includes an intracardiac EGM.

IMDs may be a part of a cardiac rhythm management system (CRM system) that includes an implantable cardiac rhythm management device (CRM device), an external interface device and a patient management computer system. An implanted cardiac rhythm management (CRM) device can be used to provide pacing therapy to a patient with sinus node dysfunction, in one example, where the heart fails to properly initiate depolarization waves, or an atrio-ventricular conduction disturbance, where the conduction of depolarization waves through the heart tissue is impaired, or to support and treat patients with many different types of cardiac issues. Examples of implantable medical devices that may be used to gather data include implantable pacemakers, implantable cardioverter defibrillators (ICDs), and devices that include a combination of pacing and defibrillation including cardiac resynchronization therapy.

A cardiac signal is a record of the heart's activity. An EGM is a recording of cardiac electrical activity represented by the voltage signal produced by one or more sensing electrodes in a cardiac device. EGM signals can be digitized and recorded by a cardiac device and then either transmitted via a telemetry link to an external programmer or stored for later transmission. The patient's cardiac activity can thus be observed in real-time or over a selected historical period for diagnostic purposes offline at a later time.

The science of morphology deals with interpretation of the shape characteristics of the cardiac signals, such as EGM signals, where such shape characteristics include amplitude, width and contour. The morphology of a cardiac waveform can be used to discriminate between different types of cardiac arrhythmias and other cardiac events, and morphology information can be very useful to clinicians treating the patient.

IMD System

FIG. 1 is an illustration of portions of a system that uses an implanted medical device (IMD) 110. Other types of cardiac rhythm management (CRM) devices may also be used including external medical devices. Examples of IMDs 110 include, without limitation, a pacer, a defibrillator, a cardiac resynchronization therapy (CRT) device, or a combination of such devices. The system also typically includes an IMD programmer or other external device 170 that communicates wireless signals 190 with the IMD 110, such as by using radio frequency (RF) or other telemetry signals.

The IMD 110 is coupled by one or more leads 108A-C to the heart 105. Cardiac leads 108A-C include a proximal end that is coupled to IMD 110 and a distal end, coupled by an electrode or electrodes to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

The heart 105 includes a right atrium 100A, a left atrium 100B, a right ventricle 105A, a left ventricle 105B, and a coronary sinus extending from right atrium 100A. The atrial lead 108A includes electrodes (electrical contacts, such as ring electrode 125 and tip electrode 130) disposed in the right atrium 100A of heart 105 for sensing signals, or delivering pacing therapy, or both, to the right atrium 100A.

The ventricular lead 108B includes one or more electrodes, such as tip electrode 135 and ring electrode 140, for sensing signals, delivering pacing therapy, or both sensing signals and delivering pacing therapy. The lead 108B optionally also includes additional electrodes, such as for delivering atrial cardioversion, atrial defibrillation, ventricular cardioversion, ventricular defibrillation, or combinations thereof to the heart 105. Such electrodes typically have larger surface areas than pacing electrodes in order to handle the larger energies involved in defibrillation. The lead 108B optionally provides resynchronization therapy to the heart 105.

The IMD 110 may include a third cardiac lead 108C attached to the IMD 110 through the header 155. The third cardiac lead 108C includes ring electrodes 160, 165 placed in a coronary vein lying epicardially on the left ventricle (LV) 105B via the coronary vein 120.

The lead 108B may include a first defibrillation coil electrode 175 located proximal to tip and ring electrodes 135, 140 for placement in a right ventricle (RV), and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD can 150. This improves defibrillation by delivering current from the RV coil 175 more uniformly over the ventricular myocardium. In some examples, the therapy is delivered from the RV coil 175 only to the electrode formed on the IMD can 150.

Other forms of electrodes include meshes and patches which may be applied to portions of heart 105 or which may be implanted in other areas of the body to help "steer" electrical currents produced by IMD 110. The present methods and systems will work in a variety of configurations and with a variety of electrical contacts or "electrodes." Sensing among different sets of electrodes often provides directional information regarding the propagation of cardiac signals and is often referred to as sensing among different vectors. For example, in a single chamber ICD, sensing from a right ventricular tip electrode 135 to a right ventricular ring electrode 140 would be a first vector, and sensing from an RV coil 175 to an electrode on the can 150, or a header 155, would be second vector. Various electrode configurations may be used, as described in co-pending and commonly-assigned U.S. Publication No. 2010/0204745, filed Jan. 26, 2010, the contents of which are herein incorporated by reference.

The electrode configuration used in the systems and methods described herein allow for the collection of EGMs on at least one channel, while multiple channels may be used. In one embodiment, signals from a first and second channel of an EGM are analyzed. When electrodes are implanted in or near an atrium, a signal from an atrial channel is provided. A ventricular EGM signal is recorded with electrodes implanted in or near a ventricle, called a ventricular channel. For example, a ventricular channel or vector may include a tip electrode and ring electrode for the right ventricular channel or ring electrodes for the left ventricular channel. The atrial and ventricular channels are also sometimes referred to as rate channels because they can be used to sense the heart's depolarization rate. Another channel, known as the shock channel or shock vector, may be used. The shock channel is sensed using electrodes that are also used to delivery high-energy shock therapy. In one example, the shock channel includes an electrode placed at the superior vena cava (SVC). In another example, the shock channel includes an electrode placed in the RV.

Description of Noise, Undersensing, and Oversensing

The sensing of signals by the IMD 110 may be susceptible to noise. The signal noise may be physiologic or non-physiologic in nature. Non-physiologic signal noise may be intracardiac in origin due to a separate electronic device providing electrical therapy. The IMD 110 may sense the therapy. Intracardiac non-physiologic signal noise may also be due to the sensing electrode or lead making electrical contact with an abandoned lead fragment.

Non-physiological noise can also be extracardiac (external to the heart) in origin. The noise may be due to the device itself, such as due to fracture of an IMD lead, a faulty set screw or adapter used for securing an IMD lead, or electronic "chatter" picked up by the IMD lead. Non-physiologic noise sources separate from the IMD include electrocautery during surgery, magnetic resonance imaging, a lithotripsy procedure, or transmissions from electronic surveillance equipment.

Physiologic noise can also be intracardiac or extracardiac in origin. Examples of intracardiac physiologic noise includes a low amplitude R-wave or a prolonged Q-T segment of a sensed cardiac activation signal that complicates identification of a T-wave, and dislodgement of a ventricular lead that complicates the sensing and identifying of a P-wave or causes double-counting of an R-wave.

Extracardiac physiologic noise includes oversensing of abdominal or diaphragmatic myopotentials (DMPs). DMPs are electrical activation signals related to contractions of the diaphragm. DMPs may be sensed by the IMD due to the position of implanted leads used to sense cardiac depolarization or due to failure of the insulation of the implanted leads. In the absence of a lead abnormality, oversensing of noise that leads to inappropriate delivery of cardioverting or defibrillating shock therapy is most commonly due to DMPs. The DMPs are incorrectly identified by an IMD as ventricular tachyarrhythmia, such as ventricular fibrillation (VF) or VT for example. Consequently, accurately discriminating DMPs from actual arrhythmias reduces delivery of inappropriate shocks from devices with cardioverter/defibrillator capability.

Undersensing is an intrinsic depolarization that is present but not seen or sensed by the device. In a pacemaker, undersensing may be caused by inappropriately programmed sensitivity, lead dislodgment, lead failure (i.e. insulation break, conductor fracture), lead maturation, or change in the native signal. Oversensing is the sensing of an inappropriate signal, which can be either physiologic or non-physiological. Where oversensing occurs, the channel signal may not correspond with the electrogram pattern of the other channel from the same chamber. Oversensing may be caused by lead insulation failure, lead fracture, or a lead connection problem.

Figure 2:
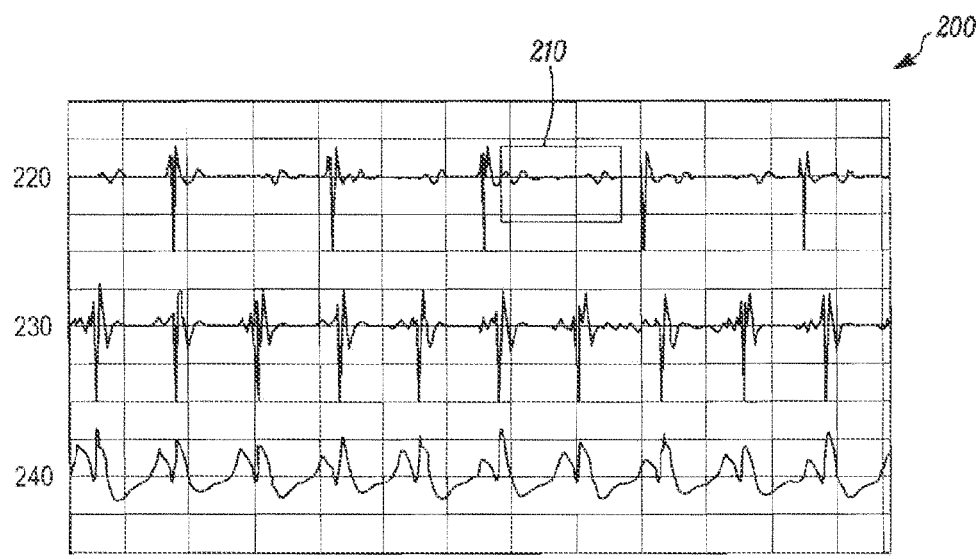
FIG. 2 is an electrogram showing an example of far-field sensing on the right atrial (RA) channel.

Other factors are also of concern with cardiac devices. Generally, the larger the detected signal, the better. In certain devices, if the signal passed through the right ventricular (RV)

lead (R wave) is too small, then a pacemaker or other IMD may not sense intrinsic rhythm and begin pacing inappropriately, creating a risk for arrhythmia. Furthermore, if the R wave is too small and a particular device is programmed to account for small signals, there is a possibility that the lead will detect a signal that is not ventricular activity and incorrectly not pace the ventricle when the patient is potentially asystolic. In the case of the right atrial (RA) lead, both the size of the signal sensed on the RA lead (P wave) and the presence of distant but detectable ventricular activity are significant. The distant ventricular activity that is still detected by the atrial lead is known as far-field sensing. The EGM 200 of FIG. 2 shows an example far-field signal 210 on the right atrial (RA) channel 220. The ventricular channel 230 and shock channel 240 are also shown on the EGM 200. If far-field activity is too large relative to an atrial signal, an IMD may sense both the far-field and the atrial signal and determine that both are atrial signals, counting two beats instead of one. The methods described herein seek to detect and remove far-field signals to improve the accuracy of beat detection.

Representative Electrograms

An implantable cardiac device configured with one or more sensing channels and associated circuitry for recording and storing electrograms is programmed to generate representative electrograms with respect to time and/or with respect to heart rate. A representative electrogram may be a single electrogram recorded during a specified time or when the heart rate is within a specified range or may be an average of electrograms recorded during a discrete time interval. Averages may be computed as moving averages of electrograms recorded either continuously or periodically during a discrete time interval or when the heart rate is within a specified range. The representative electrograms may reflect either intrinsic or paced cardiac electrical activity, or separate representative electrograms may be derived from intrinsic and paced beats. A set of representative electrograms may be downloaded to an external programmer (or other external device), which can then graphically display the downloaded representative electrograms as an aggregate indexed with respect to time or heart rate. In one embodiment, rather than being reviewed real-time, electrograms may alternatively be downloaded and reviewed off-line. In another embodiment, electrograms are reviewed by a processor within an implanted device after the electrograms are stored on memory within the implanted device.

The method described herein is used to analyze the electrograms to improve beat detection and to detect undersensing, oversensing, and noise.

Independent Event Sensing Algorithm

In one embodiment, electrograms from multiple channels are gathered. While data from many different channels can be used and compared, the following example discusses an algorithm using data gathered from the RV and shock channels. Furthermore, while this method may be performed in real-time, electrograms may also be analyzed off-line.

Removal of Far-Field Sensing

Removal of far-field sensing from a group of candidate beats is provided in one embodiment.

Figure 3:
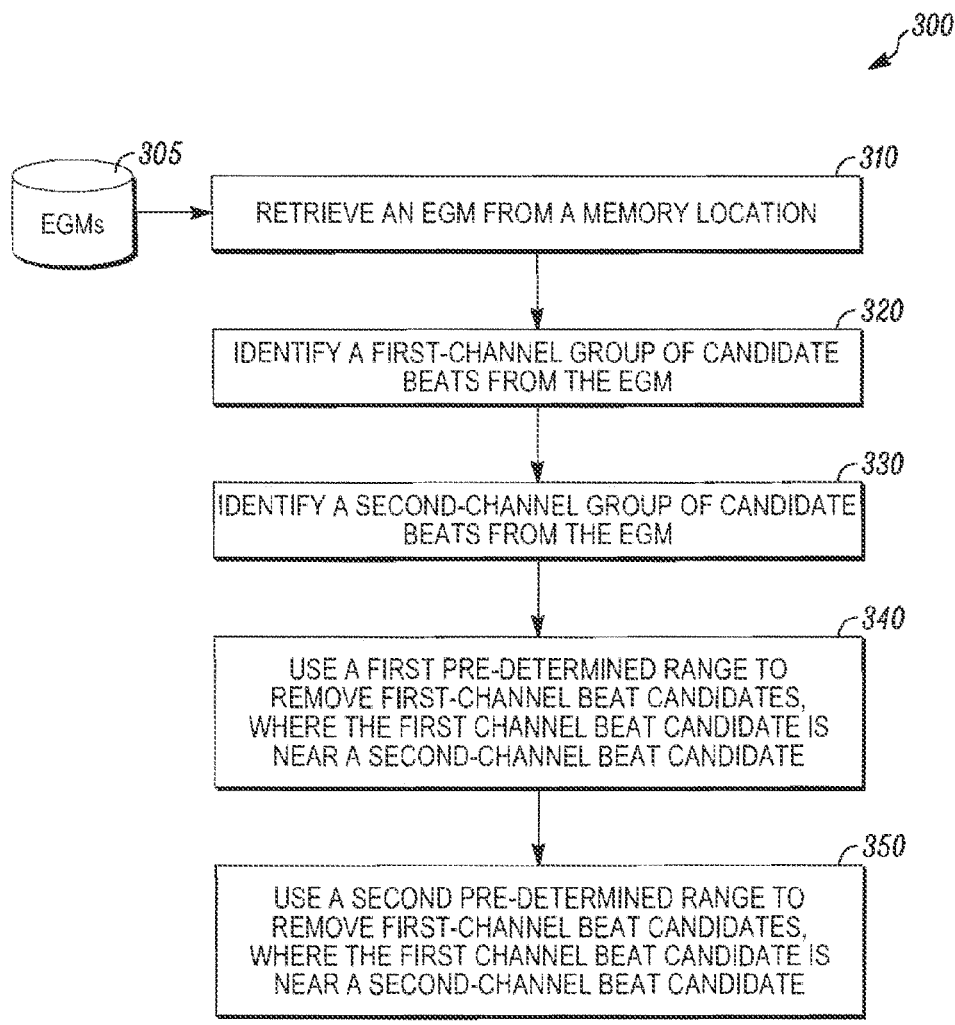
FIG. 3 is a flowchart showing an off-line method for analyzing cardiac electrogram data.

In one embodiment, the far-field removal is performed on cardiac electrogram data off-line rather than real-time. Performing the far-field removal off-line allows for the electrogram data to be run through and analyzed multiple times. Hence, the method is known as a "multi-pass" method. In each pass or data analysis run, each candidate beat is examined and different criteria are applied to remove candidate beats that should not be considered heart beats. One example of the multi-pass method 300 with two total passes is shown in FIG. 3. FIG. 3 is flowchart showing an off-line method for analyzing cardiac electrogram data.

In step 310, an electrogram is retrieved from a memory location 305 by a computer or other computing device. In step 320, at least one channel from the electrogram is analyzed to identify a first-channel group of candidate beats. In a first embodiment, this channel is the atrial channel. In other embodiments, the ventricular or shock channels may be used. Next, in step 330, at least one other channel from the electrogram is analyzed to identify a second-channel group of candidate beats. In the first embodiment, this channel is the ventricular channel. In other embodiments, this channel may be the atrial or shock channel. Processes for identifying candidate beats will be further described herein.

The first and second channels are then used in a multi-pass process for the purpose of removing far-field sensing. In a first pass 340, a first pre-determined range is used to remove first-channel beat candidates. During the first pass 340, the amplitude of each first-channel beat candidate is compared to the amplitude of both the previous and next first-channel beat candidate. Each first-channel beat candidate is evaluated to see if it meets the following criteria: the amplitude of a first-channel beat candidate is outside of a first pre-determined range from either the previous or the next beat and the first-channel beat candidate is near a second-channel beat candidate. In some embodiments, if the number of first-channel beat candidates which meet the criteria exceeds a first pre-defined beat count threshold, the first-channel beat candidates that meet the criteria are determined not to be a beat and removed. The pre-determined range is used to define acceptable thresholds for beat detection. In one embodiment, the first pre-determined range is between 20% to 200% of the amplitude from the previous beat or the next beat. In other embodiments, the first pre-determined range may be 10% to 250% of the amplitude from the previous or the next beat. A first-channel beat candidate is considered to be "near" a second-channel beat candidate if it occurs within a first time interval from the second-channel beat candidate. In one embodiment, that first time interval is 50 milliseconds. In other embodiments, that time interval is 100 milliseconds. The first pre-defined beat count threshold is used to define minimum number of beats that meet the pre-defined criteria. In one embodiment, the first pre-defined beat count threshold is 10% of the total number of beat candidates. In another embodiment, the first pre-defined beat count threshold is 5% of the total number of beat candidates.

In a second pass 350 of the multi-pass process, a second pre-determined range is used to further remove first-channel beat candidates. During the second pass 350, the amplitude of each remaining first-channel beat candidate is compared to the amplitude of both the previous and next first-channel beat candidate. Each first-channel beat candidate is evaluated to see if it meets the following criteria: the amplitude of a first-channel beat candidate is outside of a second pre-determined range from either the previous or next beat and the first-channel beat candidate is near a second-channel beat candidate. If the number of first-channel beat candidates which meet the criteria exceeds a second pre-defined beat count threshold, the first-channel beat candidates which meet the criteria are determined not to be a beat and removed. In one embodiment, the second pre-determined range is defined as beats with amplitudes that are between 40% to 180% of the amplitude of the previous candidate beat or the next candidate beat. In other embodiments, the second pre-determined range may be between 50% to 150% of the amplitude of the previous and next candidate beat. In one embodiment, the second pre-defined beat count threshold is 20% of the total number of beat candidates. In another embodiment, the second pre-defined beat count threshold is 30% of the total number of beat candidates.

Figure 4:
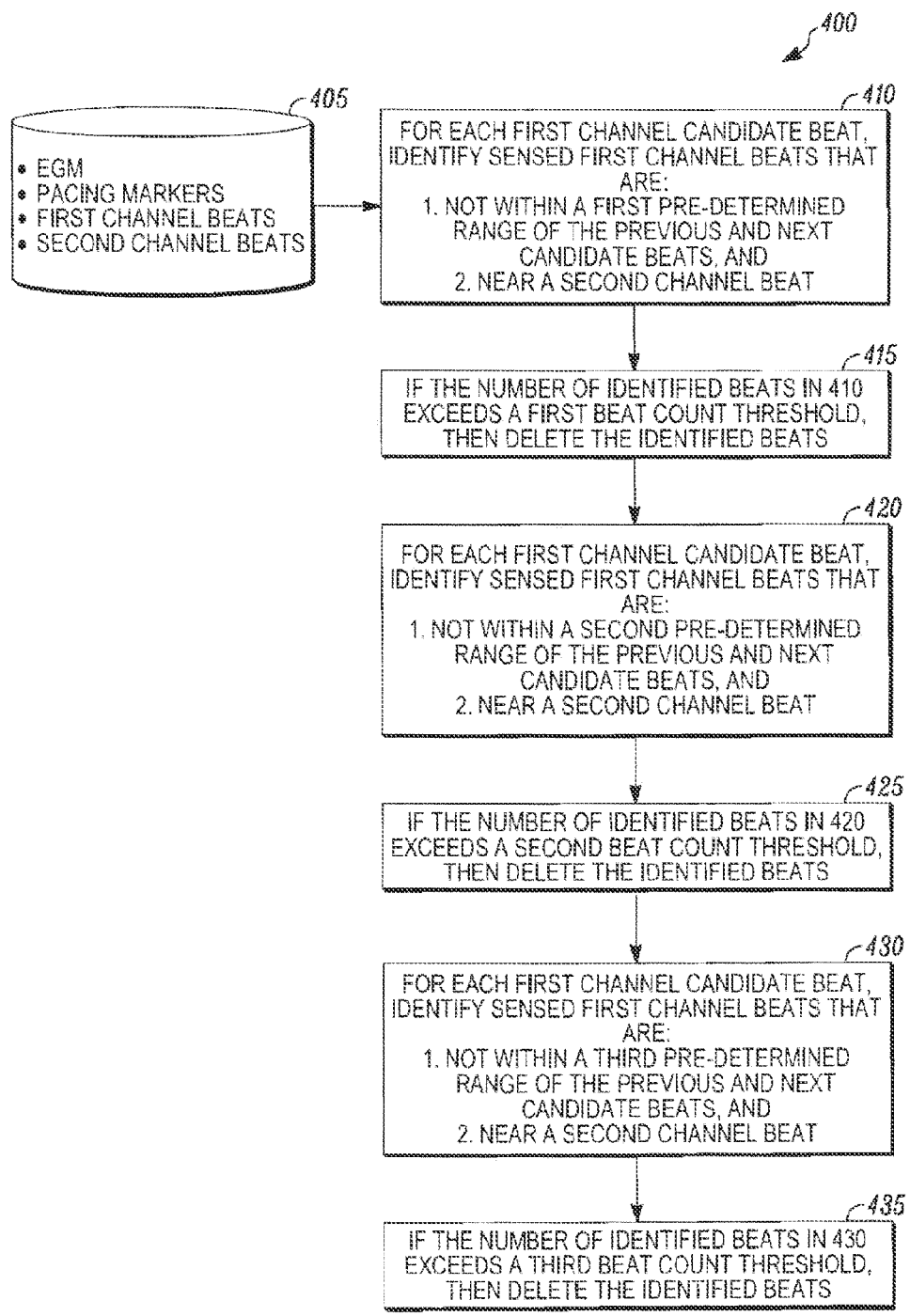
FIG. 4 is a flowchart of an embodiment of a multi-pass method.
Figure 5:
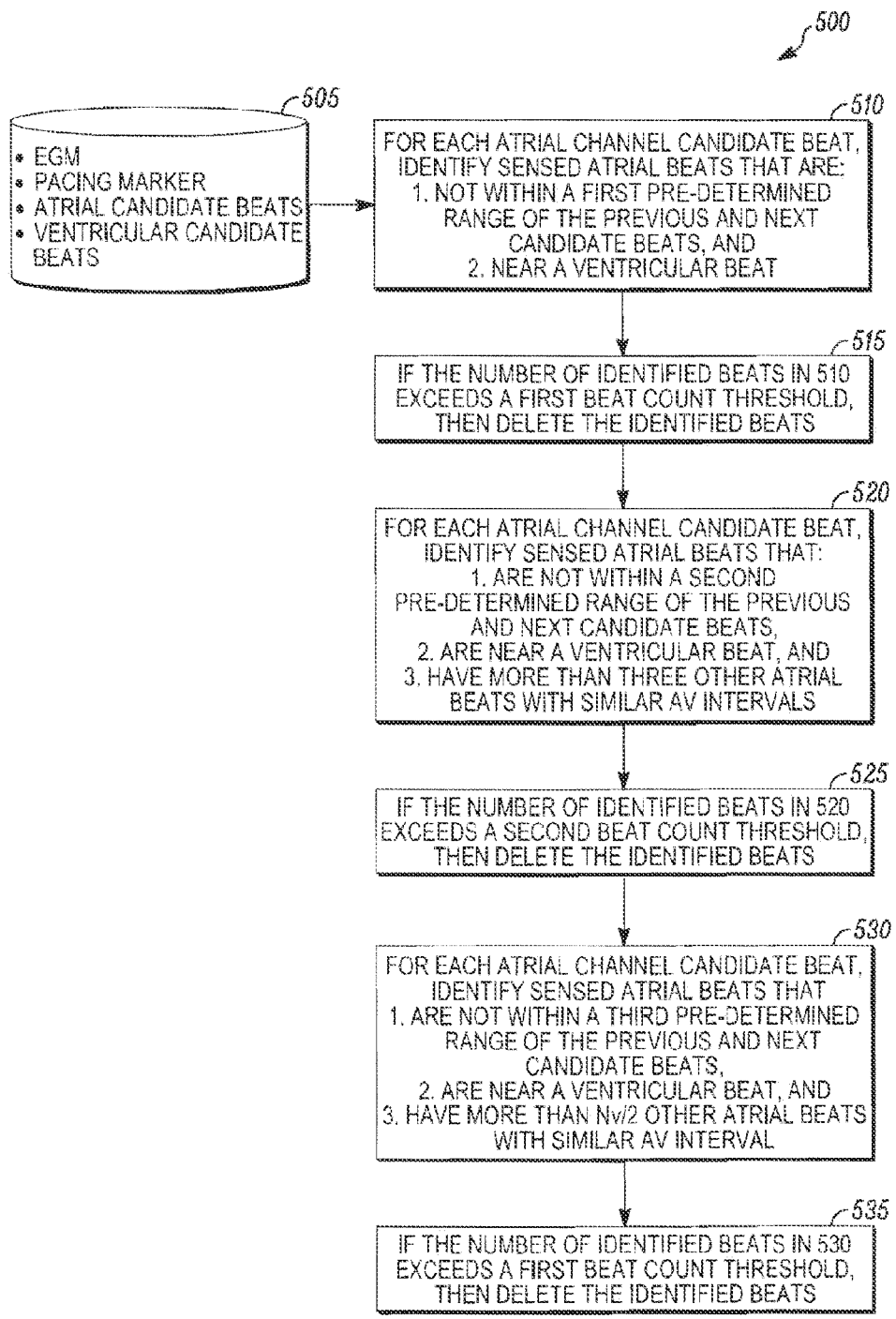
FIG. 5 is a flowchart of an alternative embodiment of a multi-pass method for use with atrial and ventricular beats.

Other embodiments of a multi-pass method for removal of far-field sensing are shown in FIGS. 4 and 5. In some embodiments, more than two passes are used in a multi-pass method, as shown in FIGS. 4 and 5. For example, in the multi-pass method 400 shown in FIG. 4, first 410 and second passes 420 are used followed by a third pass 430. After each of steps 410, 420, and 430, the number of identified beats is compared to a first, second, or third beat count threshold in steps 415, 425, and 435, respectively. In step 415, if the number of identified beats exceeds a first beat count threshold, then the identified beats are deleted. In step 425, if the number of identified beats exceeds a second beat count threshold, then the identified beats are deleted. In step 435, if the number of identified beats exceeds a third beat count threshold, then the identified beats are deleted.

In the multi-pass method 400, a memory 405 storing electrograms, pacing markers, first-channel beat candidates, and second-channel beat candidates provides data to be analyzed. The data is analyzed through the first 410 and second 420 passes, similar to the multi-pass method 300 of FIG. 3. In the third pass 430, a first-channel beat candidate is removed if it is near a second-channel beat and outside of a third pre-determined range from either the previous or next beat and near a second channel beat and the number of beat candidates which meet the criteria exceeds a third pre-determined beat count threshold. In one embodiment, the third pre-determined range is defined as between 80% and 120% of amplitude from the previous or next candidate beat. In other embodiments, the third pre-determined range may be defined as 70% or 130% of amplitude from the previous or next candidate beat. In one embodiment, the third pre-defined beat count threshold may be 40% of total number of beats. In another embodiment, the third pre-defined beat count threshold may be 50% of the total number of beats.

In the multi-pass method 500 shown in FIG. 5, an atrial channel is used as a first-channel, and a ventricular channel is used as a second-channel. A memory 505 provides storage for electrograms, pacing markers, atrial beat candidates and ventricular beat candidates to be analyzed. Similar to the embodiment shown in FIG. 4, the first pass 510 in FIG. 5 analyzes each sensed atrial candidate beat and removes sensed atrial candidate beats that are a) not within a first-predetermined range of the previous and next atrial candidate beats and b) near a ventricular beat. In certain embodiments, certain passes may have one or more additional requirements that must be met before first-channel candidate beats are removed, as shown in the second pass 520 and third 530 pass in FIG. 5. For example, one pass may have a further requirement that there are at least a predetermined number of similar beats with similar first/second channel intervals in order for first-channel beat candidates to be removed, as with steps 520 and 530. The first/second channel interval is defined as the time difference between a first channel beat and the closest second channel beat. For example, in an embodiment where the first channel is an atrial channel and the second channel is a ventricular channel, shown in FIG. 5, the first/second channel interval is the AV interval, which is defined as the time difference between the atrial beat to the closest ventricular beat. In order for there to be a certain number of "similar" beats with similar AV intervals (or first/second channel intervals, generally), a similarity threshold is defined. The similarity threshold may be, for example, 5 milliseconds. In another embodiment, the similarity threshold may be 10 milliseconds. In such an embodiment, it may be required that there be, for example, three or more other atrial beats with similar AV intervals. As shown in the second pass 520 of FIG. 5, assuming the AV interval of the beat is x milliseconds, it is required then that more than three other atrial beats can be found, any of whose AV interval is within 10 milliseconds less than x and 10 milliseconds more than x. While FIG. 5 shows this requirement in the second pass, it may be a requirement of any or all of the passes of the multi-pass method.

A similar criterion is applied in the third pass 530, but the number of required similar beats is different. Before a candidate beat is removed, it is required that there are more than $N_V/2$ atrial beats with similar AV intervals, where $N_V$ is defined as the total number of ventricular beats (or the total number of beats on the second channel, if another type of channel is used). Where the similarity threshold is 10 milliseconds and the AV interval of the beat is x milliseconds, it is required that more than $N_V/2$ other atrial beats can be found, any of whose AV interval is within 10 milliseconds less than x and 10 milliseconds more than x. While FIG. 5 shows this requirement in the third pass, it may be a requirement of any or all of the passes of the multi-pass method. Any combination of requirements may also be used, as shown in FIG. 5.

In another embodiment, a fourth pass is used (not shown), similar to the first, second, and third passes, wherein the first-channel beat candidate is removed if it is near a second-channel beat and outside of a fourth pre-determined range from either the previous or next beat. Other requirements may be used, as described above.

After each of steps 510, 520, and 530, the number of identified beats is compared to a first, second, or third beat count threshold in steps 515, 525, and 535, respectively. In step 515, if the number of identified beats exceeds a first beat count threshold, then the identified beats are deleted. In step 525, if the number of identified beats exceeds a second beat count threshold, then the identified beats are deleted. In step 535, if the number of identified beats exceeds a third beat count threshold, then the identified beats are deleted.

In an off-line evaluation of the detected beats, multiple passes (i.e. more than three or four, as described above) may be performed to improve the accuracy of the method. In such an embodiment, various pre-determined thresholds are used with varying degrees of restriction. In one embodiment, the pre-determined thresholds are stricter in later passes than in early passes. For example, in one embodiment, the second pre-determined range employs a threshold of the amplitude of the neighboring beats that is higher than a threshold of the amplitude of the neighboring beats that is employed in the first pre-determined range. In another embodiment, the second pre-determined beat count threshold is greater than the first pre-determined beat count.

The multi-pass method for removing far-field sensing may also be used in conjunction with other steps, including initial beat detection, noise removal, and detecting device oversensing or undersensing.

Beat Detection on an EGM Channel

The groups of candidate beats mentioned in the multi-pass methods described herein may be acquired using beat detection algorithms described herein. These groups of candidate beats originate from any EGM channel (i.e. right or left atrial, right or left ventricular, shock). The groups of candidate beats can be used for the first-channel group of candidate beats or second-channel group of candidate beats or any other channel group of candidate beats. In one embodiment, a particular group of candidate beats will originate from a single channel of an EGM.

Figure 6:
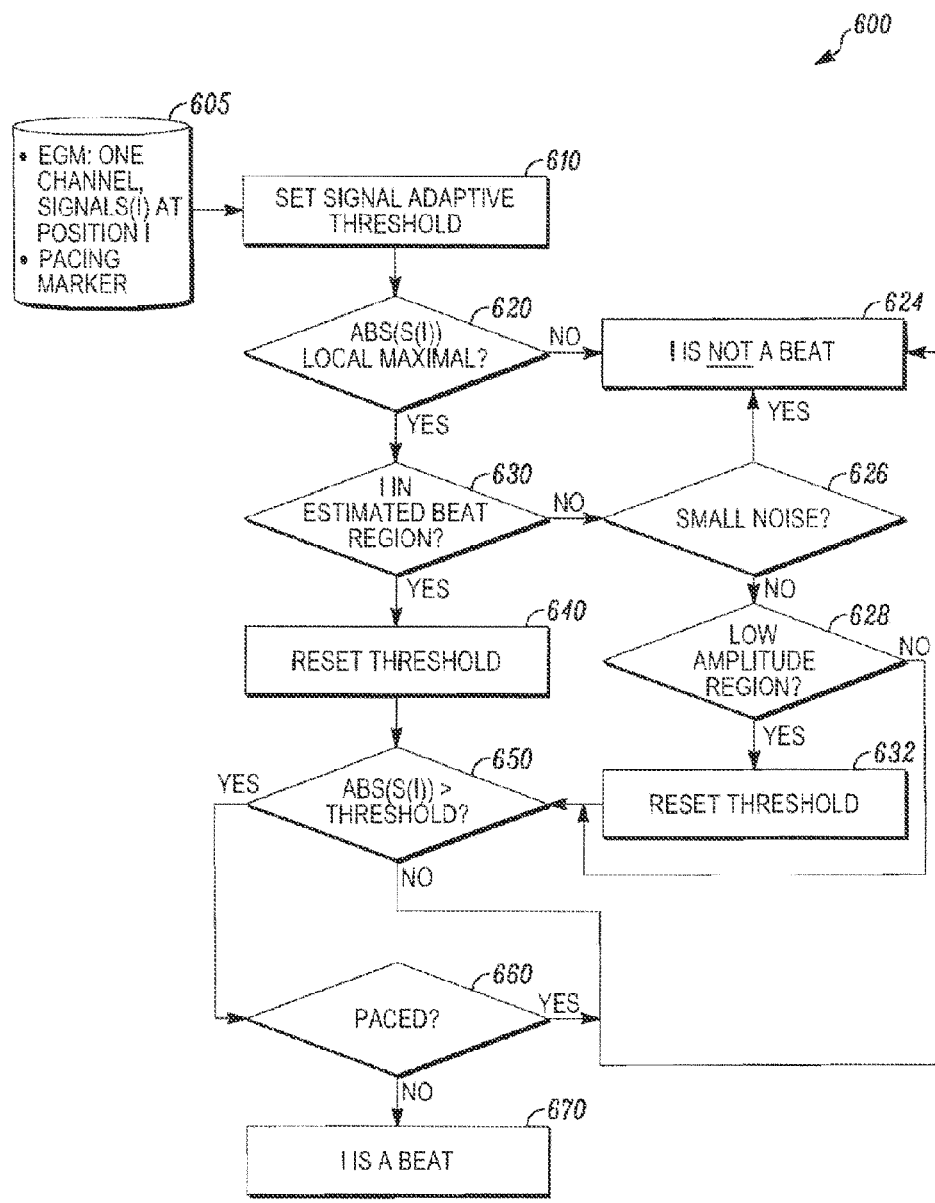
FIG. 6 is a flowchart showing one embodiment of beat detection on one channel of an electrogram.

A flow chart showing an example of beat detection sensing on one channel of an EGM 600 is shown in FIG. 6. The method takes at least one channel from an EGM and pacing markers 605 from a memory storage location and analyzes the signal from the at least one channel to detect and collect a group of beats. First in step 610, a first signal adaptive threshold is set. In one embodiment, the first signal adaptive threshold is set to 21 units. In another embodiment, the first signal adaptive threshold is set to 0.2 mV. The EGM channel data will be referred to as the signal S, where S(i) is the signal value at a position i on the EGM channel signal. Next, at step 620, at a position i, the absolute value of the signal S(i) is tested to determine if it is a local maxima. If not, the method moves to step 624 and the signal at location is determined not to be a beat. If the absolute value of the signal S(i) is a local maxima, step 630 is performed at i to determine whether it is located within an estimated beat region. In one embodiment, the "estimated beat region" is defined as $0.8<(i-p)/(p-q)<1.2$, where p is the position of the previous beat, and q is the position of the beat occurring before p. In one embodiment, every data sample in the EGM is examined to determine whether it could be a beat location. In another embodiment, beat detection is performed on small (i.e. 100 ms), non-overlapping segments of the EGM.

Figure 7:
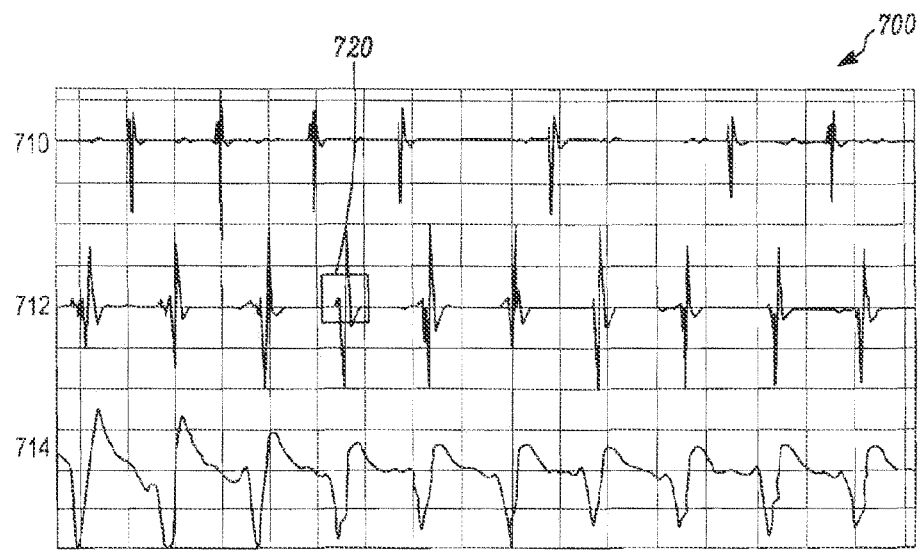
FIG. 7 shows an electrogram where an example estimated beat region is labeled (above) and an electrogram where an example low amplitude region is labeled (below).
Figure 7:
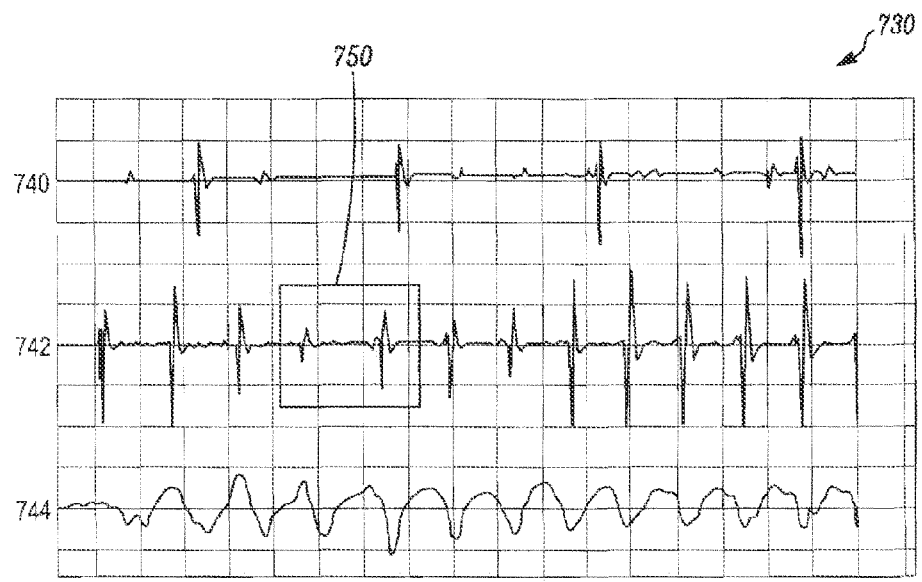

An EGM 700 with three signal channels (atrial 710, ventricular 712, and shock 714) is shown in FIG. 7. An example estimated beat region for a particular position i is shown at portion 720 of the EGM ventricular channel 712. Now referring back to FIG. 6, if i is not located in the estimated beat region, the method moves to step 626 and S(i) is analyzed to determine whether it is small noise. "Small noise" is identified if there is another signal whose absolute amplitude is larger than twice the absolute value of S(i) within a small noise interval. In one embodiment, the small noise interval is 80 milliseconds. If S(i) is a small noise, the method moves to step 624 and S(i) is declared not to be a beat. If S(i) is not a small noise, the method moves to step 628 and i is analyzed to determine whether it is located in a low amplitude region. A "low amplitude region" is identified when the magnitude of the maximum value (or the absolute value of the minimum value) within a certain interval, known as a low amplitude interval, is smaller than the first signal adaptive threshold. For example, a "low amplitude region" may be defined when the magnitude of the maximum value (or the absolute value of the minimum value) within the low amplitude interval is less than the signal adaptive threshold for the channel. That is, if the first signal adaptive threshold is 21 units, a low amplitude region is present if the magnitude of the maximum value (or the absolute value of the minimum value) within the low amplitude interval is less than 21. In one embodiment, the low amplitude interval is 400 milliseconds.

FIG. 7 also shows a portion of an EGM 730 with three signal channels (atrial 740, ventricular 742, and shock 744). An example low amplitude region is shown at portion 750 of the ventricular channel 742 of the EGM. In this embodiment, the low amplitude region is a 400 millisecond portion of the EGM 730 where i is at the center of the low amplitude region.

Again referring back to FIG. 6, if S(i) is a local maxima and in the estimated beat region, the method moves to step 640 and the first signal adaptive threshold is reset. For example, the first signal adaptive threshold may be reset to 33.3% of the amplitude of the previous beat. If the signal S(i) is not small noise and i is located in a low amplitude region, then the method moves to step 632 and the first signal adaptive threshold is reset. In one embodiment, in step 632, the first signal adaptive threshold is reset based on the maximal amplitude in the low amplitude region. For example, the first signal adaptive threshold may be reset to 95% of the maximal amplitude of the low amplitude region. In one embodiment, the low amplitude region may be 400 milliseconds. In either case, regardless of whether i is located in a low amplitude region, the absolute value of S(i) is compared to the reset first signal adaptive threshold at step 650. If the absolute value of S(i) is not greater than the threshold, the method moves to step 624 and S(i) is declared not to be a beat. If the absolute value of S(i) is greater than the threshold, the algorithm moves to step 660 and determines whether the signal at S(i) is paced and therefore caused by an artificial or device-induced shock. The determination of whether the signal at S(i) is paced is based on the input pacing markers. If the signal at S(i) is paced, S(i) is not an intrinsic beat at step 624. If S(i) is not paced, then S(i) is determined to be an intrinsic beat at step 670.

While specific values are used to determine beats in the methods described herein, many other parameters may also be used. The values described above are presented as examples and are not meant to be limiting.

Figure 8:
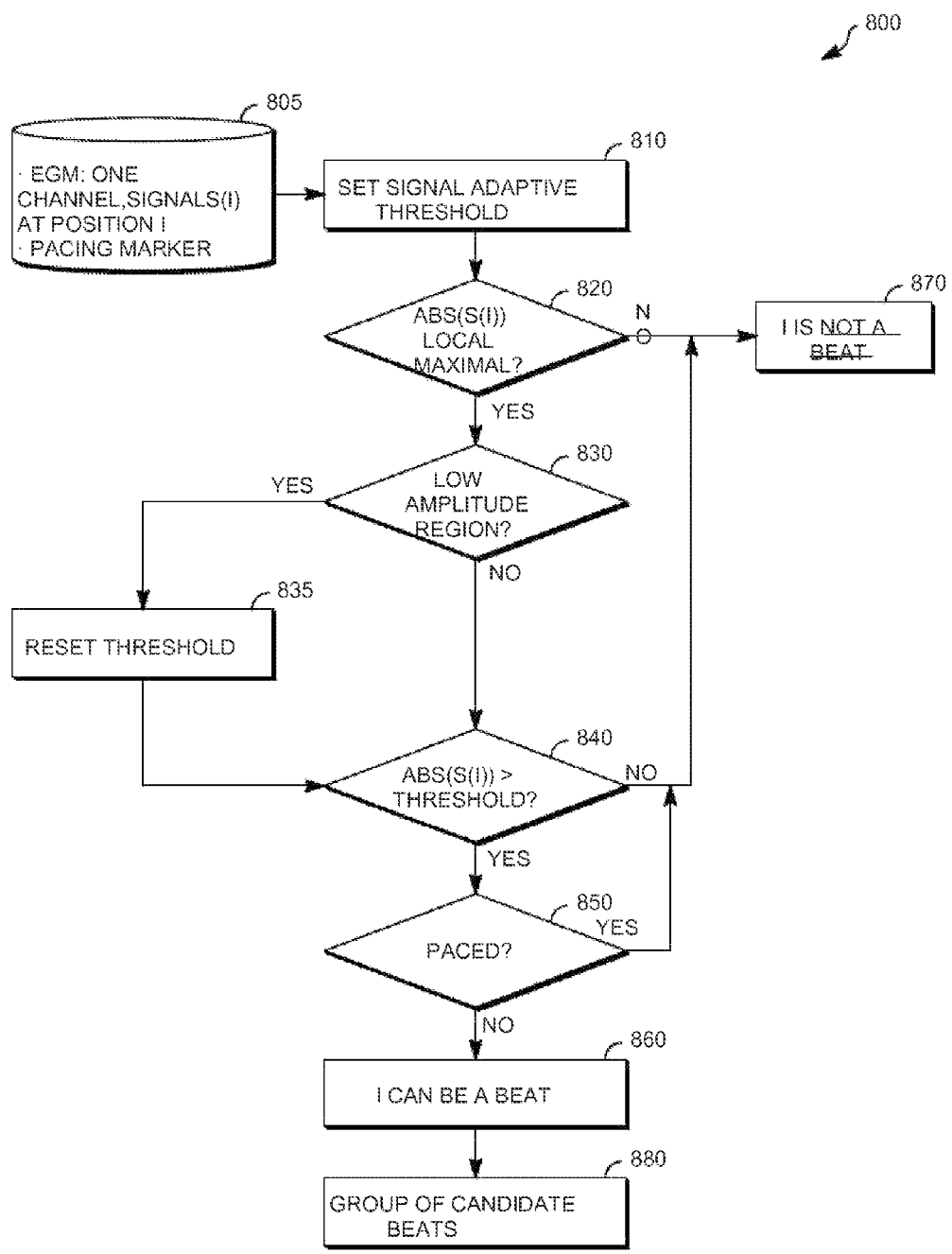
FIG. 8 is a flowchart showing another embodiment of beat detection on one channel of an electrogram.

One alternative embodiment of the method used for initial beat detection 800 is shown in FIG. 8. The method takes at least one channel from an EGM and pacing markers 805 from a memory storage location and analyzes the signals from the at least one channel to detect and collect a group of beats. First, in step 810 a signal adaptive threshold is set. In one embodiment, the threshold is set to 21 units. Then in step 820, the absolute value of the signal S(i) at position i is tested to determine whether it is a local maxima. If it is not a local maximal, the signal is determined not to be a beat at step 870.

If S(i) is a local maxima, step 830 tests the signal to determine if it is in a low amplitude region. A "low amplitude region" is identified when the magnitude of the maximum value (or the absolute value of the minimum value) within a certain interval, known as a low amplitude interval, is smaller than a signal adaptive threshold for a second rate channel. In one embodiment the second channel is the atrial channel. If the signal adaptive threshold is 21, a low amplitude region present if the magnitude of the maximum value (or the absolute value of the minimum value) within the low amplitude interval is less than 21. In one embodiment, the low amplitude interval is 400 milliseconds. If S(i) is in a low amplitude region, the adaptive threshold is reset at step 835. In one embodiment, in step 835, the signal adaptive threshold is reset based on the maximal amplitude in the low amplitude region. For example, the first signal adaptive threshold may be reset to 66% of the maximal amplitude of the low amplitude region. In one embodiment, the low amplitude region may be 400 milliseconds.

In either case, the absolute value of S(i) is tested to determine whether its value is greater than the adaptive threshold 840. If not, S(i) is not a beat 870. If the absolute value of S(i) is greater than the adaptive threshold, the algorithm determines whether the signal at S(i) is paced 850 and therefore caused by an artificial or device-induced shock. If yes, S(i) is not an intrinsic beat 870. If S(i) is not paced, then S(i) is an intrinsic beat 860 and is added to the group of candidate beats 880.

To ensure all potential beats are identified, the adaptive threshold can also be adjusted to a lower value as described above. In one embodiment, it could be 70% of the threshold described above.

These methods of detecting heart beats on at least one channel output of a group of candidate beats can then be used in combination with the far-field sensing removal techniques described above. In one embodiment, the beat detection is performed first on the RA rate channel, and then the far-field sensing is removed from this channel.

Evaluation of Event Sensing by an IMD

Figure 9:
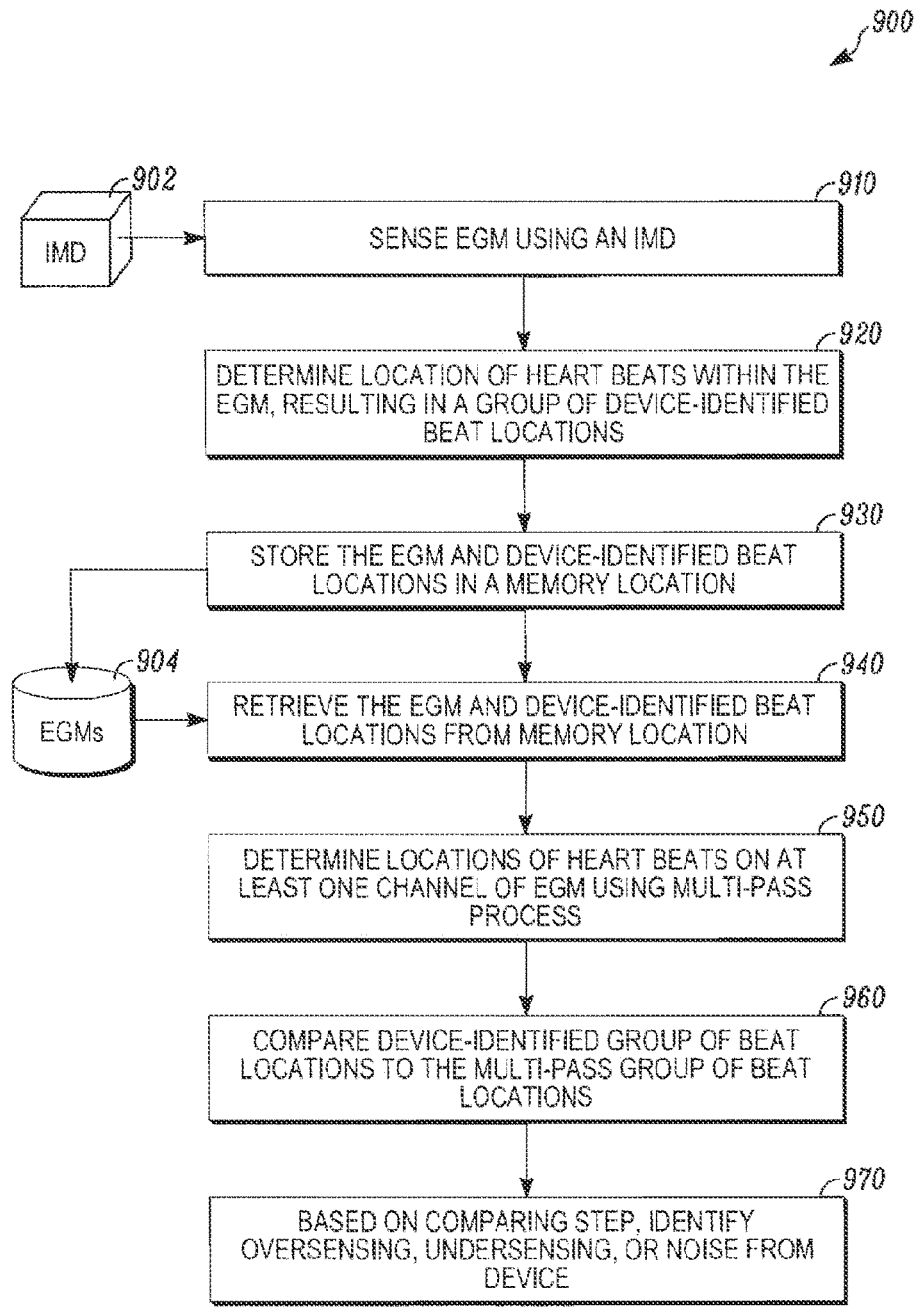
FIG. 9 is a flowchart showing one embodiment of an independent, off-line evaluation of event sensing for collected electrograms.

FIG. 9 shows a method for performing independent, off-line evaluation of event sensing for collected electrograms 900. An IMD 902 is used to sense EGM data 910. The IMD 902 determines locations of heart beats within the EGM data, resulting in a group of device-identified beat locations 920. These may also be known as device markers. Pacing markers may also be present within the EGM data, indicating when the IMD provided a pacing pulse to the patient's heart. For purposes of this discussion, pacing markers are not considered a type of device-identified beat locations. The EGM data and device-identified beat locations are then stored 930 in a memory location 904. Next, a computer or other computing device such as a programmer is used to retrieve the EGM data and device-identified beat locations from the memory location 940. The computing device determines the locations of heart beats on at least one channel of EGM data using a multi-pass process 950. The group of beat locations determined using this multi-pass process is referred to as the multi-pass group of beat locations. The computing device then analyzes and compares the device-identified group of beat locations with the multi-pass group of beat locations 960. Based on the comparison, the presence of oversensing, undersensing, or noise from the device can potentially be identified 970.

Figure 10:
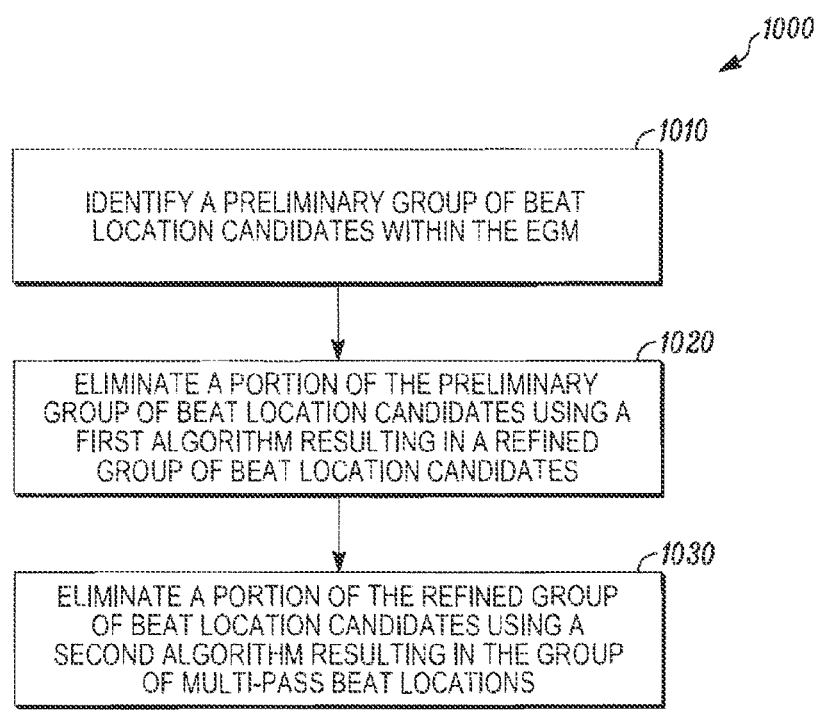
FIG. 10 is a flowchart of an alternative embodiment of a multi-pass method.

One embodiment of the multi-pass process of step 950 is shown in the flow chart of FIG. 10. In step 1010 of the multi-pass process 1000, first a preliminary group of beat location candidates within the EGM is identified by the computing device. In a first pass 1020, a portion of the preliminary group of beat location candidates is eliminated using a first algorithm, resulting in a refined group of beat location candidates. In a second pass 1030, a portion of the refined group of beat location candidates is eliminated using a second algorithm, resulting in the group of multi-pass beat locations. The second algorithm is different than the first algorithm. For example, the second algorithm may implement the same formulas but utilize different parameters. Alternatively, the second algorithm may utilize the same parameters as the first algorithm but implement different steps. The multi-pass methods described above, such as those shown in FIGS. 3, 4, and 5 and described in the accompany text, may also be used in the method for performing independent, off-line evaluation of event sensing for collected electrograms 900.

Undersensing/Oversensing/Noise Detection Results

After the number of detected beats is determined using the multi-pass methods described above, algorithms for detecting undersensing, oversensing, or CRM device noise may be implemented. These algorithms may be implemented off-line with previously recorded data. A comparison is made between the number of beats detected by the CRM device ("device-identified group of beats") and the number of sensed beats using the multi-pass methods described above ("multi-pass group of beats"). The multi-pass group of beats can be from any channel of an EGM. If the number of device-identified beats is less than the number of beat candidates by a certain threshold, device undersensing is present.

For example, in one embodiment where the algorithm is performed off-line, if the CRM device identifies fewer than 80% of the beats detected using the multi-pass method, the CRM device may be undersensing. Similarly, if the CRM device senses more than 120% of the number of beats detected using the multi-pass method, the CRM device may be oversensing.

Figure 11A:
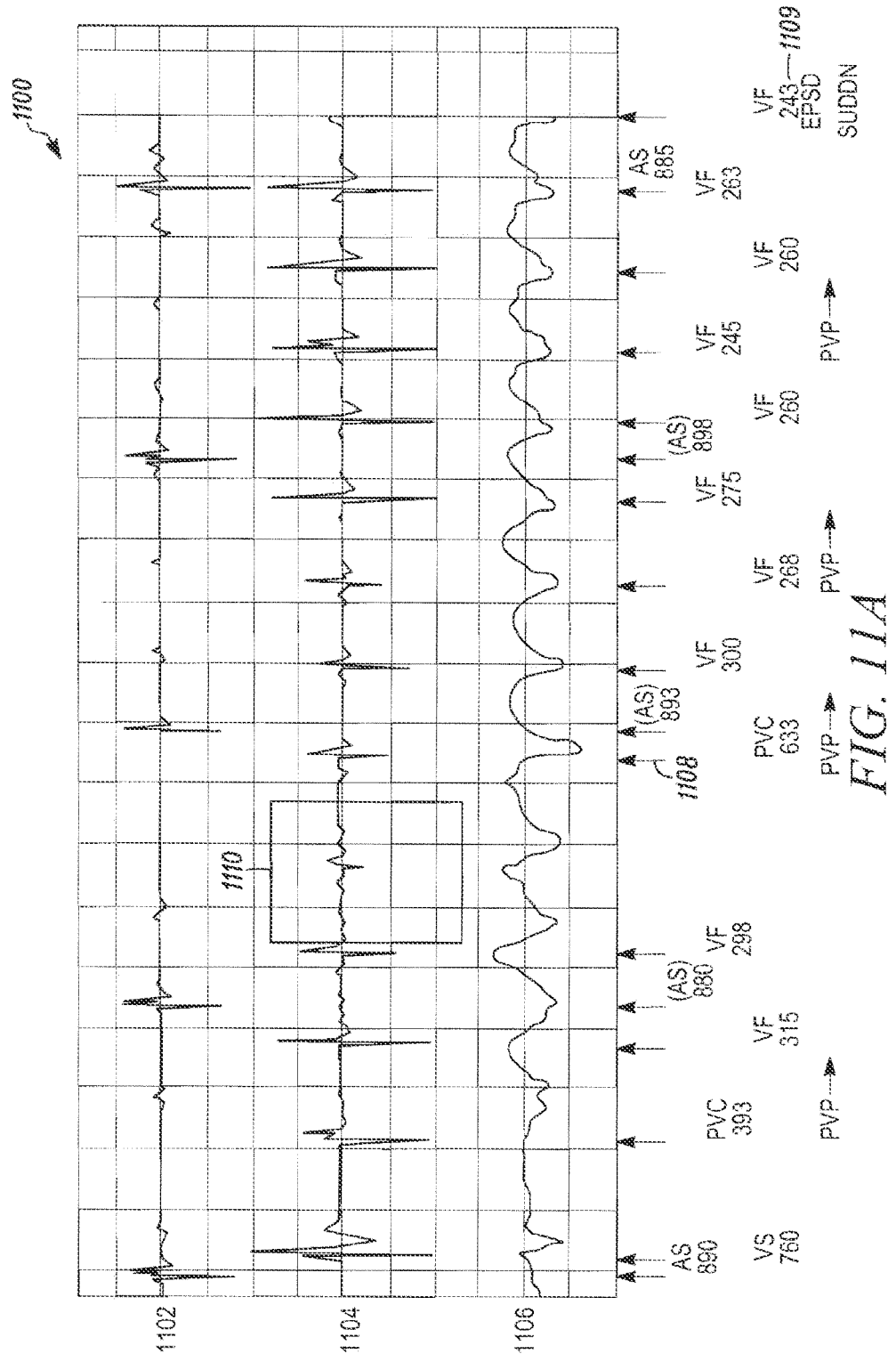
FIG. 11A shows an electrogram with data sensed by a CRM device.
Figure 11B:
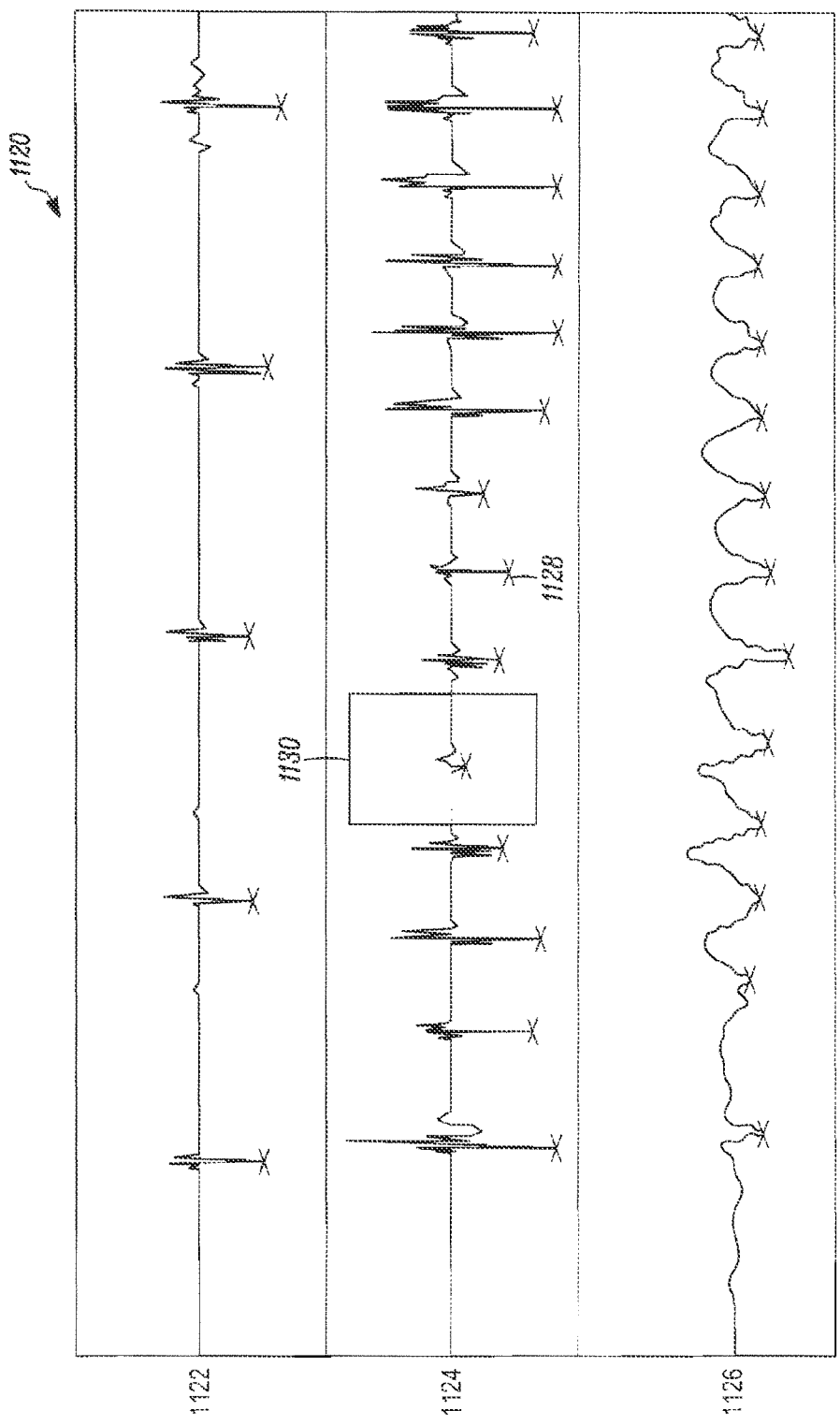
FIG. 11B shows an electrogram using the data from FIG. 11A that is further analyzed to show where beats are detected using an off-line multi-pass algorithm to reduce undersensing in accordance with an embodiment of the invention.

A comparison showing undersensing sensed by a CRM device versus a multi-pass algorithm is shown in FIGS. 11A and 11B. FIG. 11A shows an EGM 1100 from a CRM device. FIG. 11B shows output 1120 of the off-line multi-pass algorithm, where the same EGM 1100 of FIG. 11A was used as input to the off-line multi-pass algorithm. The CRM device EGM 1100 shows signals from three channels: atrial 1102, ventricular 1104, and shock 1106. Detected beats as determined by the CRM device are indicated along the bottom of the EGM using upward pointing arrows, such as arrow 1108. The signal output 1120 from the off-line multi-pass algorithm also shows signals from the three channels: atrial 1122, ventricular 1124, and shock 1126. Detected beats are indicated on the EGM with a cross mark, such as cross mark 1128 on each of the three channels.

As shown in the CRM device EGM 1100, the CRM sensing misses a beat at EGM portion 1110 (no upward arrow is present to indicate a beat is detected) on the ventricular channel 1104. In the off-line multi-pass algorithm output 1120 of FIG. 11B, output portion 1130 corresponds to the same timeframe as EGM portion 1110 in FIG. 11A. The off-line multi-pass algorithm detects the beat at portion 1130 on the ventricular channel 1124 as indicated by the cross mark in portion 1130. In some algorithms, a certain number of beats of a certain type must be sensed before an episode is declared. As a result of missing the beat at 1110, the device delayed declaring a ventricular fibrillation episode until a later beat was detected. The EGM 1100 in FIG. 11A shows a declaration of a ventricular fibrillation episode at label 1109 at the bottom right corner of FIG. 11A. However, if the beat at portion 1110 had been correctly sensed, an episode would have been properly declared at an earlier time. FIG. 11B shows the beat that was missed at portion 1110 in FIG. 11A properly sensed at portion 1130 and marked with a cross mark. As undersensing is avoided, episodes are less likely to be declared late.

Figure 12A:
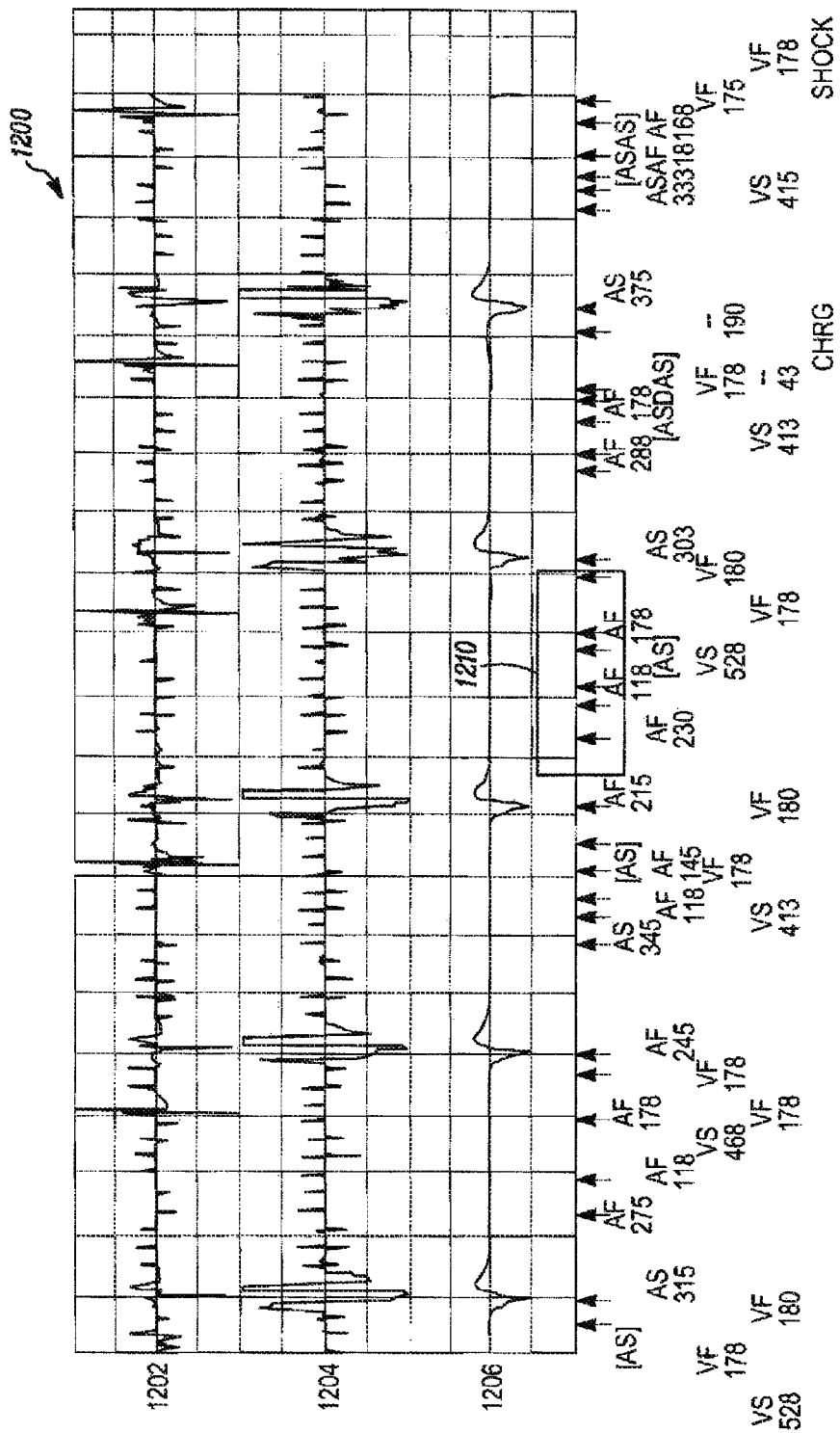
FIG. 12A shows an electrogram with data sensed by a CRM device.
Figure 12B:
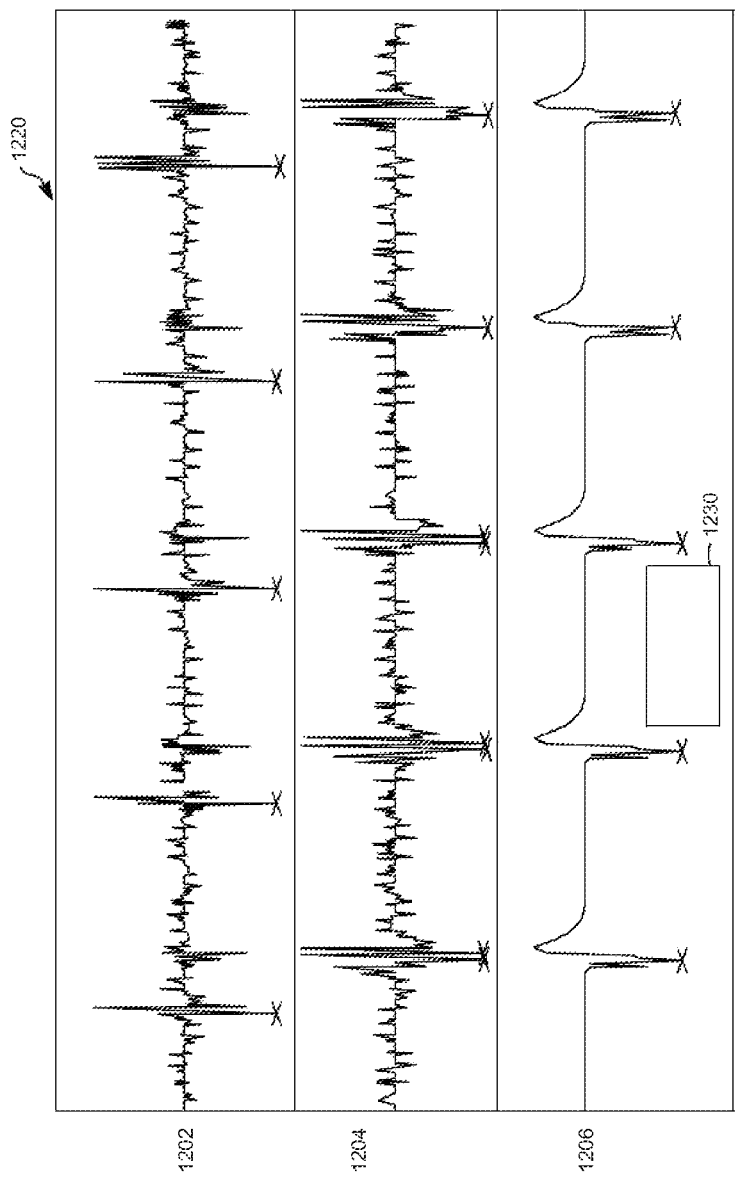
FIG. 12B shows an electrogram using the data from FIG. 12A that is further analyzed to show where beats are detected using an off-line multi-pass algorithm to reduce oversensing in accordance with an embodiment of the invention.

If the number of device-identified beats is more than the number of beat candidates by a certain threshold, device oversensing is possible. A comparison showing oversensing and noise sensed by a device versus the presently disclosed algorithm is shown in FIGS. 12A and 12B. The CRM device EGM 1200 shows signals from three channels: atrial 1202, ventricular 1204, and shock 1206. As with FIG. 11A, detected beats in FIG. 12A are indicated along the bottom of the EGM 1200 using upward pointing arrows. FIG. 12B shows output 1220 from a multi-pass off-line detection algorithm, where EGM 1200 from FIG. 12A was the input to the algorithm. Beats that are declared by the algorithm on FIG. 12B are indicated on the output 1220 with a cross mark.

FIG. 12A shows a number of detected beats in a portion 1210 of the EGM 1200 that are not in fact beats but rather the result of oversensing by the device. Portion 1230 on the algorithm output 1220 generally corresponds to the same timeframe as the position 1210 on the EGM 1200. In portion 1230 of FIG. 12B, there are no beats as determined by the algorithm. Portion 1230 of FIG. 12B therefore shows oversensing by the device and shows no detected beats at portion 1230. This evaluation can be performed over a complete EGM or for part of an EGM.

Noise in the CRM can be detected by checking the discrepancy in the number of beats detected by the CRM device and the number of sensed beats using the multi-pass methods described above. Discrepancies in the morphology, as described in common-assigned application Ser. No. 12/879,147, the content of which is herein incorporated by reference, may also be compared to detect noise in the signal. When morphology is utilized to detect noise in the signal, the change in morphology is measured by the Euclidean distance.

Other methods can optionally be incorporated into the noise detection algorithm (e.g. prior to cross-channel/rate-shock comparison). For example, noise detection based on zero-crossing count may be used, as described in U.S. Pat. No. 6,917,830, the content of which is herein incorporated by reference. Alternatively, a signal saturation check based on determining the occurrence and number of max AD count value reached can be used to detect noise.

Sources of Cardiac Signal Data

Different cardiac rhythm management devices may be used to obtain EGM data from a patient. One example of a data-generating device is an implantable cardiac rhythm management device. Specific implantable cardiac rhythm management devices include a pacemaker, a cardioverter-defibrillator, a cardiac resynchronization device, a heart rhythm monitoring device, or the like. Other implantable data-generating devices include pressure sensors, heart sound sensors and impedance sensors. However, it is also possible to generate EGM data from external devices, including external pacemakers, external cardioverter-defibrillators, external resynchronization devices, external pressure sensors, external heart sound monitors and external impedance sensors. Additional examples of external devices that monitor cardiac activity include ambulatory electrocardiography devices or Holter monitors, which continuously monitor electrical activity of the heart for 24 hours or more. A data-generating device is one that is capable of providing cardiac signal information about an episode or time period experienced by a particular patient.

Many types of CRM devices communicate with devices located outside of the body, which can receive information from the implanted device including sensor information and information about events, such as when the implanted device has provided therapy. In some cases, the external interface device can also transmit operational parameters to an implanted CRM device, that is, program the device.

These external interface devices can be provided to a patient, often in a patient's home, and can collect information from the implanted device, and provide that information to a computer system designed to monitor the patient's status. An exemplary remote patient management system is the LATITUDE® patient management system, available from Boston Scientific Corporation, Natick, Mass. Aspects of exemplary remote patient management and monitoring systems are described in U.S. Pat. No. 6,978,182, the content of which is herein incorporated by reference in its entirety.

The existence of remote patient management systems such as the LATITUDE® patient management system has provided a large amount of data about patients with implanted medical devices. For example, these systems store patient sensor readings including EGM, pressure sensor signals, impedance signals and heart sound signals. The sensor readings can include information associated with arrhythmia episodes and other episodes experienced by the patient. These systems also store information about patient characteristics, device settings and delivery of therapy by the device.

In one embodiment, a system and method uses this storehouse of patient-related data to analyze the device performance, understand a particular patient, understand a patient population group or improve therapy provided by the device. Such a system may operate outside of the device itself, such as on a server that is not at the same location as any of the data-gathering devices. As a result, a large amount of computer processing resources and memory can be devoted to utilizing the patient-related data.

"Episode" is defined to mean activity of a patient's body within a time period of particular interest. The time period can be a time when there is abnormal activity, for example, abnormal cardiac activity. "Episode data" is defined to include sensor readings from a medical data-generating device before, during and after the episode, and can also include device settings, actions that were taken by the device and other information. According to the system described herein, an episode database stores episode data about episodes that have occurred.

One or more data-generating devices can generate episode data. The episode database may have episode data about a plurality of episodes generated by one device, or generated by multiple devices. In one embodiment, the episode database is external to any of the data-generating devices. However, in another embodiment, the episode database is located within one of the data generating devices.

Storage and Use of the Episode Data and Characterization Data

The episode data or part of the episode data for a particular episode can be analyzed using a detection algorithm to detect undersensing, oversensing, or noise. Stored episodes comprising cardiac data are analyzed to collect potential beats as beat data. Beat data from different channels can be compared and analyzed to detect undersensing, oversensing, and noise. The beat data may be stored and associated with their respective episode data. The beat data may also be stored in an output database. In some embodiments, the beat data is sent to the data-generating device to be stored. Once undersensing, oversensing, or noise is detected, then it is possible to provide patients and clinicians with many different types of reports related to the episode data. It is also possible for the system to detect undersensing, oversensing, or noise that could be indicative of issues that need to be addressed by a health care provider. Alerts may be provided when an issue is detected. Programming recommendations may also be provided, for example, to adjust sensitivity, in response to detected oversensing or undersensing.

Description of Hardware Systems

The above-described method can be implemented on various hardware systems, such as on a programmer or in a patient management system. Alternatively, the method can be implemented on a computer or other computing device. Due to its low computational complexity, the method can also be implemented on implantable medical devices.

Hardware Description

Further detailed embodiments of the hardware of the system will now be described with respect to the attached figures. The method may be applied to all device stored episodes and/or EGMs collected during regular monitoring sessions.

Figure 13:
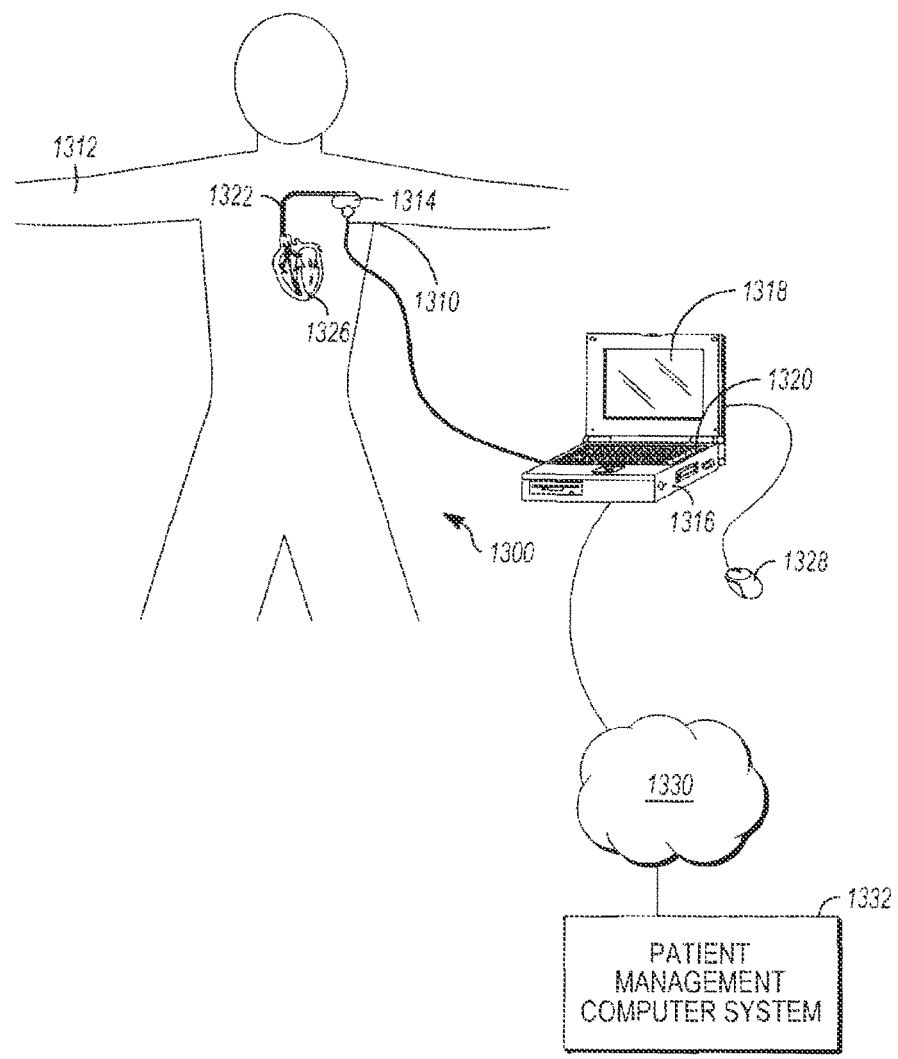
FIG. 13 is a schematic diagram of an exemplary implementation of a cardiac rhythm management (CRM) system, including an implanted CRM device, an external interface device, and a patient management computer system, consistent with at least one embodiment of the invention.

One embodiment of a data-generating device is a CRM device, as will now be described with reference to FIG. 13, which is a schematic of an exemplary CRM system 1300. The system 1300 can include an implantable medical device 1314 disposed within a patient 1312. The implantable medical device 1314 can include pacing functionality. The implantable medical device 1314 can be of various types such as, for example, a pacemaker, a cardioverter-defibrillator, a cardiac resynchronization device, a heart rhythm monitoring device, or the like. In some embodiments, the implantable medical device 1314 can include one or more leads 1322 disposed in or near the patient's heart 1326.

The implantable medical device 1314 can be in communication with an external interface system 1316. In some embodiments, communication between the implantable medical device 1314 and the external interface system 1316 can be via inductive communication through a wand 1310 held on the outside of the patient 1312 near the implantable medical device 1314. However, in other embodiments, communication can be carried out via radiofrequency transmission, acoustically, or the like.

The implantable medical device 1314 can include one or more implantable sensors in order to gather data regarding the patient 1312. For example, the implantable medical device 1314 can include an activity level sensor, a respiration sensor, a heart sounds sensor, a blood pressure sensor, an impedance sensor, or other sensors. The data gathered using the implantable medical device 1314 may be any type of patient data. In one embodiment, the implantable medical device 1314 collects electrograms from a patient. The patient data can further comprise data regarding the locations of heart beats within the electrograms. This data can be collected into groups of device-identified beat locations for each collected electrogram.

The implantable medical device 1314 can be configured to store data over a period of time, and periodically communicate with the external interface system 1316 in order to transmit some or all of the stored data.

The external interface system 1316 can be for example, a programmer, a programmer/recorder/monitor device, a computer, a patient management system, a personal digital assistant (PDA), or the like. As used herein, the term programmer refers to a device that programs implanted devices, records data from implanted devices, and allows monitoring of the implanted device. Exemplary programmer/recorder/monitor devices include the Model 3120 Programmer, available from Boston Scientific Corporation, Natick, Mass. The external interface system 1316 can include a user input device, such as a keyboard 1320 and/or a mouse 1328. The external interface system 1316 can include a video output channel and video output device, such as a video display 1318 for displaying video output. The displayed video output can include a user interface screen. In addition, the video display 1318 can also be equipped with a touch screen, making it into a user input device as well.

The external interface device 1316 can display real-time data and/or stored data graphically, such as in charts or graphs, and textually through the user interface screen. In addition, the external interface device 1316 can present textual information to a user along with several response options. The external interface device 1316 can also input and store a user's response to a question, and can store a user's text response in some embodiments.

In one embodiment, the external interface device 1316, which can also be referred to as a user interface, is in communication with a patient management computer system 1332. The communication link between the user interface 1316 and the patient management computer system 1332 may be via phone lines, the Internet 1330, or any other data connection. The user interface 1316 can also be used when it is not in communication with a device, but is only in communication with the patient management computer system 1332.

In one embodiment, the external interface device 1316 is capable of changing the operational parameters of the implantable medical device 1314, and is therefore referred to as a programmer. Typically, programmers are used to interface with CRM devices in a clinic or hospital setting. In this context, the user of the external interface device is a physician or trained technician.

Figure 14:
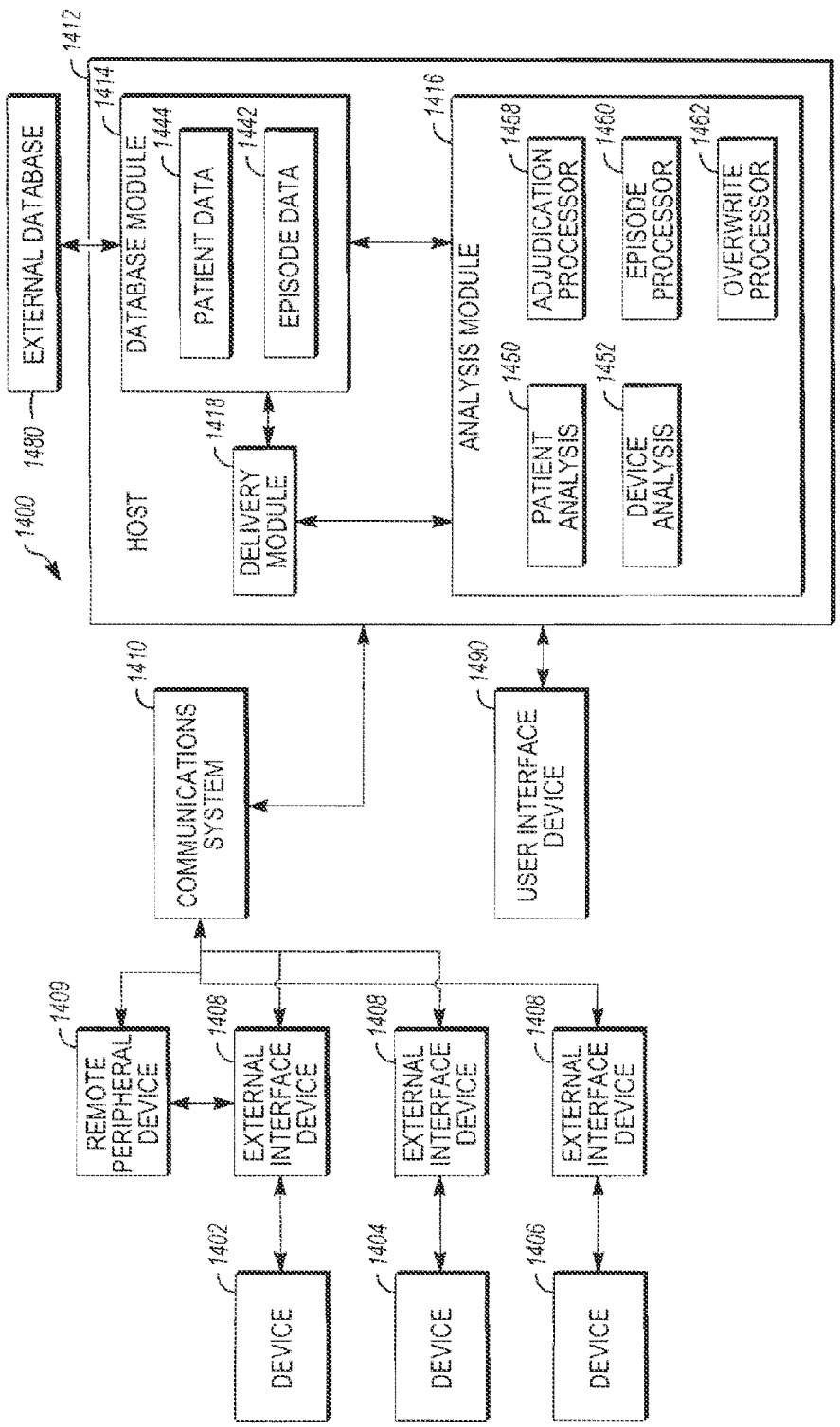
FIG. 14 is a schematic illustration of a patient management system consistent with at least one embodiment of the invention.

FIG. 14 is a schematic illustration of a patient management system consistent with at least one embodiment of the invention. The patient management system is capable of maintaining an episode database using computer storage medium. Of note, the episode database may also be present in an implantable or implanted device as discussed further herein. A computer storage medium is any technology, including devices and materials, used to place, keep and retrieve data. Examples of computer storage medium include random-access memory (RAM), a network-attached storage device, magnetic storage such as hard disk drives, optical discs, and a redundant array of independent discs (RAID). Patient management system 1400 generally includes one or more devices 1402, 1404, and 1406, one or more external interface devices 1408, a communication system 1410, one or more remote peripheral devices 1409, and a host 1412. The host 1412 may be a single computing device, such as a programmer or other patient management device. In some embodiments, the host 1412 is an external device that communicates directly with the one or more devices 1402, 1404, and 1406 and does not require the use of separate external interface devices 1408. In some embodiments, the host is an external device and receives data, such as EGM data, from an external database 1480.

Each component of the patient management system 1400 can communicate using the communication system 1410. Some components may also communicate directly with one another. The various components of the example patient management system 1400 illustrated herein are described below. The patient management system 1400 may be a single device or comprise multiple devices. In one embodiment, the patient management system 1400 is a single external computing device.

Data-generating devices 1402, 1404, and 1406 can be implantable devices or external devices that may provide one or more of the following functions with respect to a patient: (1) sensing, (2) data analysis, and (3) therapy. For example, in one embodiment, devices 1402, 1404, and 1406 are either implanted or external devices used to measure a variety of physiological, subjective, and environmental conditions of a patient using electrical, mechanical, and/or chemical means. The devices 1402, 1404, and 1406 can be configured to automatically gather data or can require manual intervention by the patient or another person. The devices 1402, 1404, and 1406 can be configured to store data related to the physiological and/or subjective measurements and/or transmit the data to the communication system 1410 using a variety of methods, described in detail below. Although three devices 1402, 1404, and 1406 are illustrated in the example embodiment shown, many more devices can be coupled to the patient management system. In one embodiment, each of the devices 1402, 1404 and 1406 is serving a different patient. In one embodiment, two or more devices are serving a single patient.

The devices 1402, 1404, and 1406 can be configured to analyze the measured data and act upon the analyzed data. For example, the devices 1402, 1404, and 1406 can be configured to modify therapy or provide an alarm based on the analysis of the data.

In one embodiment, devices 1402, 1404, and 1406 provide therapy. Therapy can be provided automatically or in response to an external communication. Devices 1402, 1404, and 1406 are programmable in that the characteristics of their sensing, therapy (e.g., duration and interval), or communication can be altered by communication between the devices 1402, 1404, and 1406 and other components of the patient management system 1400. Devices 1402, 1404, and 1406 can also perform self-checks or be interrogated by the communication system 1410 to verify that the devices are functioning properly. Examples of different embodiments of the devices 1402, 1404, and 1406 are provided herein.

Devices implanted within the body have the ability to sense and communicate as well as to provide therapy. Implantable devices can provide direct measurement of characteristics of the body, including, without limitation, electrical cardiac activity (e.g., a pacemaker, cardiac resynchronization management device, defibrillator, etc.), physical motion, temperature, heart rate, activity, blood pressure, breathing patterns, ejection fractions, blood viscosity, blood chemistry, blood glucose levels, and other patient-specific clinical physiological parameters, while minimizing the need for patient compliance. Derived measurements can also be determined from the implantable device sensors (e.g., a sleep sensor, functional capacity indicator, autonomic tone indicator, sleep quality indicator, cough indicator, anxiety indicator, and cardiovascular wellness indicator for calculating a quality of life indicator quantifying a patient's overall health and well-being).

Devices 1402, 1404, and 1406 can also be external devices, or devices that are not implanted in the human body, that are used to measure physiological data (e.g., a thermometer, sphygmomanometer, or external devices used to measure blood characteristics, body weight, physical strength, mental acuity, diet, heart characteristics, and relative geographic position).

The patient management system 1400 may also include one or more remote peripheral devices 1409 (e.g., cellular telephones, pagers, PDA devices, facsimiles, remote computers, printers, video and/or audio devices) that use wired or wireless technologies to communicate with the communication system 1410 and/or the host 1412.

The database module 1414 comprises memory for storing patient data. The patient data can include electrogram data, which comprises groups of device-identified beat locations for the electrogram data. This data may be received from a patient device, such as an implantable medical device, or it may be retrieved from another database 1480. The example database module 1414 includes a patient database 1444 and an episode database 1442, which are described further below. The patient database 1444 includes patient specific data, including data acquired by the devices 1402, 1404, and 1406, such as electrogram data, as well as a patient's medical records and historical information. The episode database 1442 has episode data regarding a plurality of different episodes generated from those of devices 1402, 1404, and 1406 that provide episode data. The episode database 1442 may also store data analyzed by the analysis module 1416.

Information can also be provided from an external source, such as external database 1480. For example, the external database 1480 could include external medical records maintained by a third party, such as drug prescription records maintained by a pharmacy, providing information regarding the type of drugs that have been prescribed for a patient or, in another example, authorization data from patient groups that have authorized users to view arrhythmia episode data. The external database 1480 may also store patient data that was previously acquired by an implantable or external medical device. One example of stored patient data on an external database 1480 is electrogram data.

The example analysis module 1416 includes a patient analysis module 1450 and a device analysis module 1452. Patient analysis module 1450 may utilize information collected by the patient management system 1400, as well as information for other relevant sources, to analyze data related to a patient and provide timely and predictive assessments of the patient's well-being. Device analysis module 1452 analyzes data from the devices 1402, 1404, and 1406 and external interface devices 1408 to predict and determine device issues or failures. For example, the device analysis module 1452 may analyze electrogram data to determine locations of heart beats on one or more channels using the multi-pass methods described above. The device analysis module 1452 can further compare device-identified beats and beat locations to beats and beat locations determined using the multi-pass method. The device analysis module 1452 can then perform comparisons to find the presence of noise, oversensing, and undersensing by the device, as described above.

The analysis module 1416 further includes an adjudication processor 1458, and episode processor 1460 and an overwrite processor 1462. In one embodiment, the adjudication processor is operatively connected to at least the episode database 1442 and is configured to receive as input episode data regarding one of the different episodes.

The episode processor 1460 performs processing of the adjudication database such as in order to provide reports, patient alerts, or programming recommendations. The overwrite processor 1462 can analyze data provided from the episode database 1442, and other portions of the patient management system 1400 to determine what particular portion of episode data for one of the episodes from the episode database should be displayed to a user. Overwrite processor 1462 can, through the delivery module 1418 described below, provide the means for graphically displaying a portion of data selected from arrhythmia episode data related to an episode of a patient, such as data generated by a data-generating device and stored in the episode database.

Overwrite processor 1462 also requests from a user any changes in the characterization data determined by the adjudication processor, and can articulate the request for user input characterizing an episode. The request may be a direct question to a user, a series of choices provided to the user, or simply a blank space on the user interface configured to accommodate the user input. The overwrite processor 1462 may also store the overwrite history for individual users.

One or more portions of the analysis module 1416, such as the adjudication processor 1458 and episode processor 1460 may be located remotely from other parts of the patient management system 1400. A microprocessor of a data-generating device may also serve as an adjudication processor in some embodiments.

Delivery module 1418 coordinates the delivery of reports, patient alerts or programming recommendations based on the analysis performed by the host 1412. For example, based on the data collected from the devices and analyzed by the host 1412, the delivery module 1418 can deliver information to the caregiver, user, or to the patient using, for example, a display provided on the external interface device 1408. A user interface device 1490 that is independent of a data-generating device may also be used to deliver information. The external interface device 1408 and user interface device 1490 are also configured, according to multiple embodiments, to display a report, alert, or programming recommendation, receive overwrite information from a user, and receive other data from the user. Displayed data, as described above, can be determined by the episode processor 1460, overwrite processor 1462 and delivery module 1418.

Figure 15:
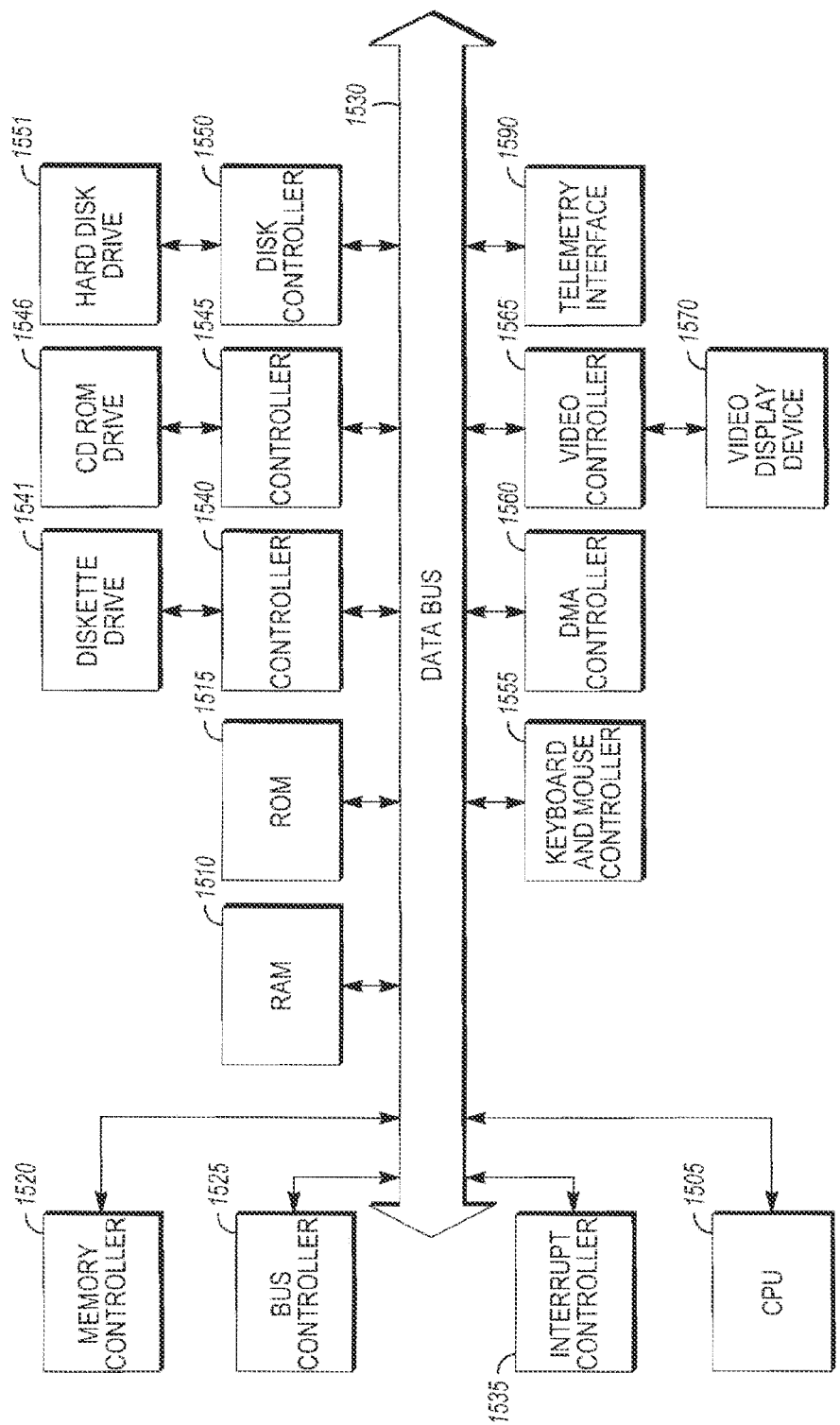
FIG. 15 is a schematic diagram of an implementation of the components of an external interface device such as a programmer, in accordance with various embodiments.

External interface devices 1408 to display information, such as programmer/recorder/monitors, can include components common to many computing devices. User interface devices 1490 to display and received information from users can also include components common to many computing devices. Referring now to FIG. 15, a diagram of various components is shown in accordance with some embodiments of the invention. However, it is not required that an external interface device have all of the components illustrated in FIG. 15.

In one embodiment, the external interface device includes a central processing unit (CPU) 1505 or processor, which may include a conventional microprocessor, random access memory (RAM) 1510 for temporary storage of information, and read only memory (ROM) 1515 for permanent storage of information. A memory controller 1520 is provided for controlling system RAM 1510. A bus controller 1525 is provided for controlling data bus 1530, and an interrupt controller 1535 is used for receiving and processing various interrupt signals from the other system components.

Mass storage can be provided by diskette drive 1541, which is connected to bus 1530 by controller 1540, CD-ROM drive 1546, which is connected to bus 1530 by controller 1545, and hard disk drive 1551, which is connected to bus 1530 by controller 1550. User input to the programmer system may be provided by a number of devices. For example, a keyboard and mouse can connected to bus 1530 by keyboard and mouse controller 1555. DMA controller 1560 is provided for performing direct memory access to system RAM 1510. A visual display is generated by a video controller 1565 or video output, which controls video display 1570. The external system can also include a telemetry interface 1590 or telemetry circuit which allows the external system to interface and exchange data with an implantable medical device. It will be appreciated that some embodiments may lack various elements illustrated in FIG. 15.

Figure 16:
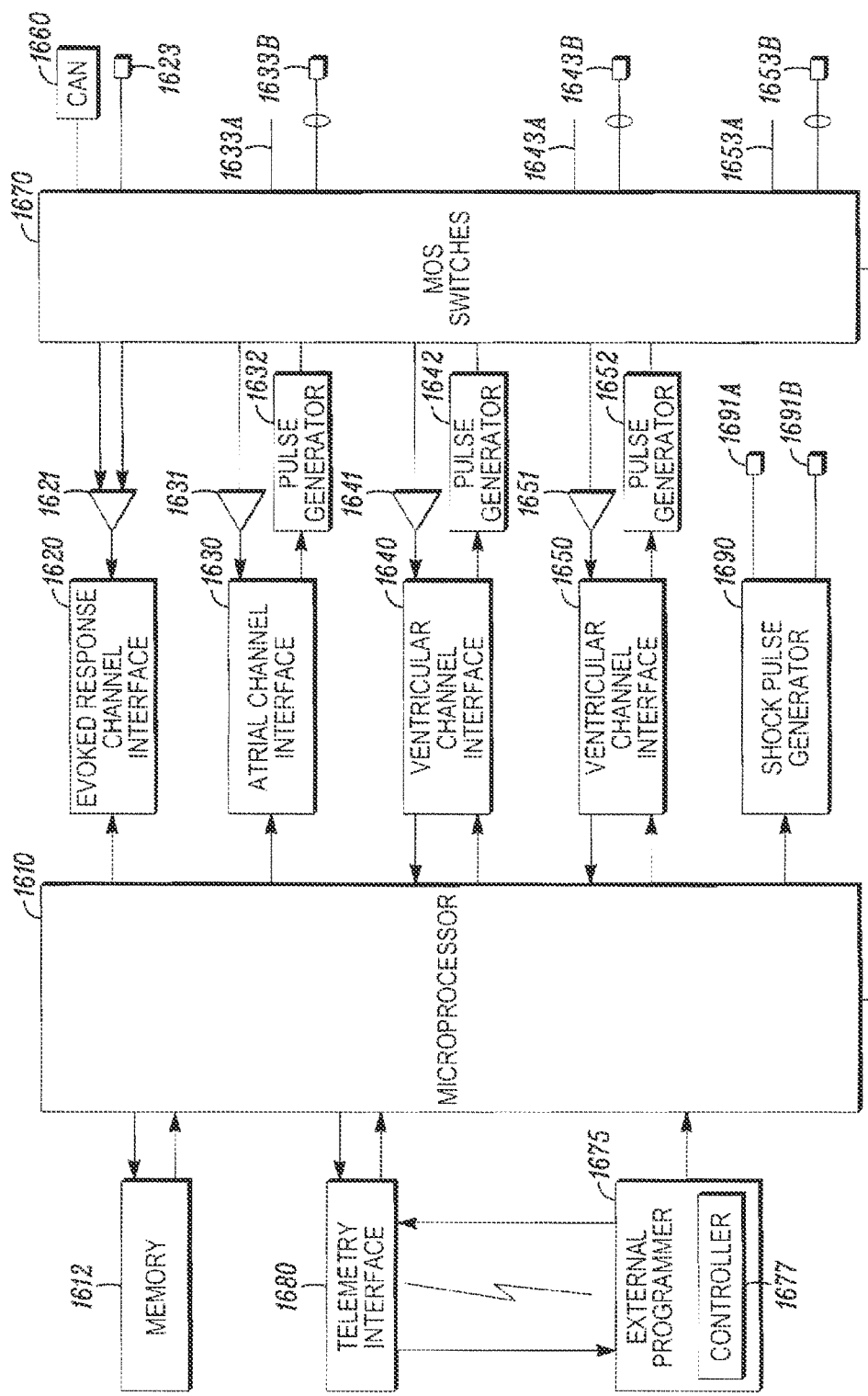
FIG. 16 is a block diagram of an implantable medical device.

Referring now to FIG. 16, some components of an exemplary implantable medical device 1600 are schematically illustrated. The implantable medical device 1600 can include a controller made up of a microprocessor 1610 communicating with a memory 1612, where the memory 1612 may comprise a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. The controller is capable of operating the implantable medical device 1600 in a number of programmed modes where a programmed mode defines how pacing pulses are output in response to sensed events and expiration of time intervals.

A telemetry interface 1680 is provided for communicating with an external programmer 1675. The external programmer is a computerized device with a controller 1677 that can interrogate the implantable medical device 1600 and receive stored data as well as adjust the operating parameters of the pacemaker.

The implantable medical device 1600 has an atrial sensing/pacing channel comprising ring electrode 1633A tip electrode 1633B sense amplifier 1631, pulse generator 1632, and an atrial channel interface 1630 which communicates bi-directionally with a port of microprocessor 1610. The device also has two ventricular sensing/pacing channels that similarly include ring electrodes 1643A and 1653A tip electrodes 1643B and 1653B sense amplifiers 1641 and 1651, pulse generators 1642 and 1652, and ventricular channel interfaces 1640 and 1650. For each channel, the electrodes are connected to the implantable medical device 1600 by a lead and used for both sensing and pacing. A MOS switching network 1670 controlled by the microprocessor is used to switch the electrodes from the input of a sense amplifier to the output of a pulse generator. A shock channel is also provided comprising a shock pulse generator 1690 and shock electrodes 1691A and 1691B that enables the device to deliver a defibrillation shock to the heart when fibrillation or other tachyarrhythmia is detected. The implantable medical device 1600 also has an evoked response sensing channel that comprises an evoked response channel interface 1620 and a sense amplifier 1621 that has its differential inputs connected to a unipolar electrode 1623 and to the device housing or can 1660 through the switching network 1670. The evoked response sensing channel may be used to verify that a pacing pulse has achieved capture of the heart in a conventional manner or, as explained below, used to record an evoked response electrogram.

The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or adjusting the pacing pulse energy by changing the pulse amplitude or pulse width. The microprocessor 1610 controls the overall operation of the device in accordance with programmed instructions stored in memory. The sensing circuitry of the implantable medical device 1600 generates atrial and ventricular sense signals when voltages sensed by the electrodes exceed a specified threshold. The controller then interprets sense signals from the sensing channels and controls the delivery of paces in accordance with a programmed pacing mode. The sense signals from any of the sensing channels of the implantable medical device 1600 in FIG. 16 can be digitized and recorded by the controller to constitute an electrogram that can either be transmitted via the telemetry link 1680 to the external programmer 1675 or stored for later transmission. The patient's cardiac activity may thus be observed in real-time or over a selected historical period.

The above-described method can be regularly initiated to evaluate the sensing performance of the medical device. Additionally, the method can also be triggered by events, such as when ventricular arrhythmia episodes are detected, when mode switch due to atrial arrhythmias occurs, and when atrial arrhythmia episodes are detected. When issues are detected, the device may store the electrogram and provide to physician for review. Programming recommendations may also be made. In some instances, arrhythmia therapy may be withheld due to detection of issues. Gathered data may be used as input for other device functionality, such as arrhythmia adjudication.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments of the invention can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this invention pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive. The scope of the present subject matter should be determined with reference to the appended claims, along with the full scope of equivalents to which such claims are entitled.

We claim:

1. An off-line method for analyzing cardiac electrogram data, comprising:
retrieving an electrogram from a memory location;
identifying a first-channel group of candidate beats from at least a first channel of the electrogram;
identifying a second-channel group of candidate beats from at least a second channel of an electrogram;
evaluating whether each first-channel beat candidate is near a second-channel beat candidate;
for each first-channel beat candidate near a second-channel beat candidate, comparing the amplitude of the first-channel beat candidate with an amplitude of a previous beat and an amplitude of a next beat on the first electrogram channel and removing first-channel beat candidates that have an amplitude that is outside of a first pre-determined range from either the amplitude of the previous beat or the amplitude of the next beat; and
for each first-channel beat candidate near a second-channel beat candidate, comparing the amplitude of the first-channel beat candidate with an amplitude of a previous beat candidate and an amplitude of a next beat candidate on the first electrogram channel and removing first-channel beat candidates that have an amplitude that is outside of a second pre-determined range from either the amplitude of the previous beat or the amplitude of the next beat candidate;
wherein a first-channel beat candidate is near a second-channel beat candidate if it occurs within a first time interval from the second-channel beat candidate.

2. The method of claim 1, wherein the first electrogram channel is an atrial channel electrogram and the second electrogram channel is a ventricular channel electrogram.

3. The method of claim 1, further comprising:
for each first-channel beat candidate of the first electrogram channel near a beat candidate from the second electrogram channel, comparing the amplitude of the first-channel beat candidate with an amplitude of a previous beat and an amplitude of a next beat on the first electrogram channel; and
removing first-channel beat candidates that have an amplitude that is outside of a third pre-determined range from either the amplitude of the previous beat or the amplitude of the next beat.

4. The method of claim 1, wherein the first-channel beat candidates further comprise locations of the first-channel beat candidates within the electrogram.

5. The method of claim 4, further comprising:
retrieving a group of device-identified beat locations within the electrogram;
comparing the group of device-identified beat locations to the locations of the remaining first-channel beat candidates; and
based on the comparing step, identifying oversensing of beats, undersensing of beats, or noise from the device.

6. The method of claim 1, wherein the first pre-determined range is between 10% and 250% of the amplitude of the previous beat or the next beat.

7. The method of claim 1, wherein the first pre-determined range is between 20% and 200% of the amplitude of the previous beat or the next beat.

8. The method of claim 1, wherein the second pre-determined range is between
40% and 180% of the amplitude of the previous beat or the next beat.

9. The method of claim 1, wherein the first time interval is 100 milliseconds.

10. An off-line method for analyzing cardiac electrogram data, comprising:
retrieving an electrogram from a memory location;
identifying an initial first-channel group of candidate beats from at least a first channel of the electrogram;
identifying a second-channel group of candidate beats from at least a second channel of an electrogram;
evaluating whether each first-channel beat candidate is near a second-channel beat candidate;
for each initial first-channel beat candidate near a second-channel beat candidate, removing candidate beats from the group of initial first-channel candidate beats that meet a set of criteria, wherein the criteria comprises:
comprising comparing the amplitude of the initial first channel beat candidate with an amplitude of a previous beat and an amplitude of a next beat on the first electrogram channel and removing initial
(a) first-channel beat candidates that have an amplitude that is outside of a first pre-determined range from either the amplitude of a previous beat or the amplitude of a next beat, and the number of first-channel beat candidates that are outside of a first pre-determined range from either the previous or next beat exceeds a first pre-defined beat count threshold; and
wherein an initial first-channel beat candidate is near a second-channel beat candidate if it occurs within a first time interval from the second-channel beat candidate.

11. The method of claim 10, wherein the first electrogram channel is an atrial channel electrogram and the second electrogram channel is a ventricular channel electrogram.

12. The method of claim 10, wherein removing candidate beats from the group of initial first-channel candidate beats that do not meet a set of criteria further comprises comparing the amplitude of the initial first-channel beat candidate with an amplitude of a previous beat candidate and an amplitude of a next beat candidate on the first electrogram channel and removing initial first-channel beat candidates that have an amplitude that is outside of a second pre-determined range from either the amplitude of the previous beat or the amplitude of the next beat candidate.

13. The method of claim 12, wherein initial first-channel beat candidates that are outside of a second pre-determined range from either the previous or next beat candidate are removed only if the number of first-channel beat candidates that are outside of the second pre-determined range from either the previous or next beat exceeds a second pre-defined beat count threshold.

14. The method of claim 11, wherein the first pre-defined beat count threshold is 10% of the initial first-channel group of candidate beats.

* * * * *